United States Patent
Munbodh

(10) Patent No.: US 11,975,217 B2
(45) Date of Patent: May 7, 2024

(54) COMPUTER-IMPLEMENTED METHOD OF EVALUATING A PROTOCOL FOR RADIATION THERAPY INCLUDING A PRE-TREATMENT PHYSICS CHART REVIEW (TPCR)

(71) Applicant: Reshma Munbodh, New Haven, CT (US)

(72) Inventor: Reshma Munbodh, New Haven, CT (US)

( * ) Notice: Subject to any disclaimer, the term of this patent is extended or adjusted under 35 U.S.C. 154(b) by 0 days.

(21) Appl. No.: 17/527,855

(22) Filed: Nov. 16, 2021

(65) Prior Publication Data
US 2022/0143423 A1 May 12, 2022

Related U.S. Application Data

(63) Continuation of application No. 16/524,896, filed on Jul. 29, 2019, now Pat. No. 11,173,323.

(60) Provisional application No. 62/711,074, filed on Jul. 27, 2018.

(51) Int. Cl.
*A61N 5/10* (2006.01)
*G16H 20/40* (2018.01)

(52) U.S. Cl.
CPC ............. *A61N 5/1031* (2013.01); *A61N 5/10* (2013.01); *A61N 5/103* (2013.01); *A61N 5/1038* (2013.01); *A61N 5/1039* (2013.01); *A61N 5/1048* (2013.01); *A61N 5/1049* (2013.01); *A61N 5/107* (2013.01); *G16H 20/40* (2018.01)

(58) Field of Classification Search
CPC ........ A61N 5/10; A61N 5/103; A61N 5/1031; A61N 5/1038; A61N 5/1039; A61N 5/1048; A61N 5/1049; A61N 5/1071

USPC .......................................................... 378/65
See application file for complete search history.

(56) References Cited

U.S. PATENT DOCUMENTS

| | | | | | |
|---|---|---|---|---|---|
| 6,546,073 | B1 * | 4/2003 | Lee | ....................... | A61N 5/1031 378/65 |
| 6,741,674 | B2 * | 5/2004 | Lee | ....................... | A61N 5/1031 378/65 |
| 6,990,175 | B2 * | 1/2006 | Nakashima | ............ | A61B 6/032 378/92 |
| 7,046,762 | B2 * | 5/2006 | Lee | ....................... | A61N 5/1031 378/65 |

(Continued)

OTHER PUBLICATIONS

Reshma Munbodha et al., Graph-based risk assessment and error detection in radiation therapy, Med. Phys., vol. 48, Issue 3: Mar. 2021, 965-977. (Year: 2021).*

*Primary Examiner* — Allen C. Ho
(74) *Attorney, Agent, or Firm* — Davis Malm D'Agostine, P.C.; David J. Powsner

(57) ABSTRACT

A computer-implemented method evaluates a protocol for radiation therapy for a target volume of a patient. The method uses a computer system executing software instructions establishing computer processes. The computer processes receiving and storing data defining the protocol and characterizing the target volume. The computer processes parse the data to extract parameters characterizing the protocol. The computer processes apply the extracted parameters and the target volume to a model that represents relationships among sub-processes and variables pertinent to execution of the protocol in a patient. The computer processes obtain from the model an evaluation of the protocol and providing the evaluation as an output.

24 Claims, 19 Drawing Sheets

(56) References Cited

U.S. PATENT DOCUMENTS

| | | | |
|---|---|---|---|
| 7,519,150 B2* | 4/2009 | Romesberg, III | A61N 5/1031 378/65 |
| 7,574,251 B2* | 8/2009 | Lu | A61N 5/1031 600/411 |
| 7,844,560 B2* | 11/2010 | Krishnan | G16H 20/40 706/46 |
| 8,238,516 B2* | 8/2012 | Sakurai | A61N 5/1048 378/65 |
| 8,804,906 B2* | 8/2014 | Roy | A61N 5/1084 378/65 |
| 8,836,697 B2* | 9/2014 | Nord | A61N 5/1031 345/419 |
| 9,087,224 B2* | 7/2015 | Jaffray | A61N 5/1045 |
| 9,155,908 B2* | 10/2015 | Meltsner | G16H 20/40 |
| 9,192,786 B2* | 11/2015 | Yan | A61N 5/1049 |
| 9,205,279 B2* | 12/2015 | Sumanaweera | A61N 5/1039 |
| 10,449,388 B2* | 10/2019 | Yin | A61N 5/103 |
| 10,475,537 B2* | 11/2019 | Purdie | A61N 5/103 |
| 11,173,323 B2* | 11/2021 | Munbodh | A61N 5/1031 |
| 11,557,390 B2* | 1/2023 | Hibbard | G16H 20/40 |

* cited by examiner

CHART REVIEW REPORT — 1505

Patient name: xxx
Patient MRN: xxx
Plan name: xxx
Course number: xx
Date: mm/dd/yyyy

1510

| Chart Review | |
|---|---|
| Treatment plan is not approved for treatment | |
| Number of constraints violated | 5 |
| Number of inconsistent variables | 7 |
| Impact score | 376 |
| Severity score | 13 |

1515

| Conflict | |
|---|---|
| 1 | IMRTQANeeded_PM is inconsistent with TreatmentModality_PM_PlanningIntent |
| 2 | DoseRate_TPS is invalid |
| 3 | DoseRate_TPS is inconsistent with DoseFractionationType_PM_PlanningIntent |
| 4 | PrescriptionDose_TPS is inconsistent with NumberOfFractions_TPS |
| 5 | NumberOfFractions_PM_PlanningIntent is inconsistent with NumberOfFractions_TPS |

1520

| Variable | Value | Module | Sub-process | Impact | Severity |
|---|---|---|---|---|---|
| Treatment Modality | 3D | Patient Manager, Planning Intent | Planning Intent and Dose Prescription | 129 | 2 |
| Dose fractionation type | Conventional | Patient Manager, Planning Intent | Planning Intent and Dose Prescription | 81 | 2 |
| Number of fractions | 10 | Patient Manager, Planning Intent | Planning Intent and Dose Prescription | 54 | 2 |
| Number of fractions | 12 | Treatment Planning System | Planning Intent and Dose Prescription | 35 | 2 |
| Prescription dose | 3000 | Treatment Planning System | Planning Intent and Dose Prescription | 35 | 2 |
| Dose rate | 1500 | Treatment Planning System | Beam Configuration | 35 | 2 |
| IMRT QA needed | Yes | Patient Manager | IMRT QA | 7 | 1 |

FIG. 15A

COMPUTER-IMPLEMENTED METHOD OF EVALUATING A PROTOCOL FOR RADIATION THERAPY INCLUDING A PRE-TREATMENT PHYSICS CHART REVIEW (TPCR)

PRIORITY

This patent application is a continuation of U.S. patent application Ser. No. 16/524,896, filed Jul. 19, 2019, now U.S. Pat. No. 11,173,323, issued which claims the benefit of U.S. provisional patent application No. 62/711,074, filed Jul. 27, 2018. The teachings of both of the aforesaid applications are hereby incorporated by reference herein.

TECHNICAL FIELD

The present invention relates to automated methods and systems for evaluation and verification of treatment plans for radiation therapy.

BACKGROUND ART

Tumor stage, grade and location and the patient's age and health determine treatment of tumor. More than 50% of patients diagnosed with cancer receive radiation therapy (RT). Radiation therapy involves the treatment of patients with ionizing radiation to eradicate cancer cells. Ionizing radiation, however, also has the potential to cause harm. This conjunction of harmful and potentially life-saving aspects necessitates the highest level of care to ensure safety and efficacy.

The aim of radiation therapy is two-fold: (1) to maximize the radiation dose delivered to the tumor to achieve local tumor control, while (2) minimizing the amount of radiation delivered to healthy tissue to minimize radiation-induced toxicity in normal tissue since radiation also damages normal tissue. Modern external beam radiation therapy (EBRT) techniques, for example, whereby a linear accelerator is used to aim high-energy ionizing radiation to the tumor from outside the body, allow the design of highly conformal radiation treatment plans. These permit high doses of ionizing radiation to be delivered to the tumor, thus maximizing local tumor control, while minimizing irradiation of surrounding normal tissue, thus reducing the likelihood of radiation-induced toxicity in normal tissue. It is important therefore to ensure that the planned radiation treatment is safe, and can be delivered to the patient as planned.

FIG. 1 illustrates the workflow steps in radiation therapy planning and delivery. These steps include radiation prescription 102, acquisition of x-ray computed tomography (CT) for treatment planning 104, treatment planning 106, physician review of treatment plan 108, pre-treatment physics chart review (TPCR) 110, treatment delivery on linear accelerator 112, and verification of delivered treatment 114.

As an example, consider EBRT for the treatment of prostate cancer. Here, prior to commencing radiation treatment, the patient's physician enters a prescription for the radiation dose to be delivered to the patient, usually in multiple fractions over several days or weeks, and dosimetric constraints limiting radiation exposure of normal tissues.

In order to create the patient-specific, prescribed radiation treatment plan, a 3D diagnostic energy (kilovoltage) CT scan of the patient's pelvis is then acquired for treatment planning purposes. The planning CT gives accurate three-dimensional anatomical information about the patient's bony and soft tissue anatomy, enabling delineation of the clinical target volume (CTV) and other anatomically relevant organs and structures. The CTV encloses the gross tumor volume (GTV) and also accounts for microscopic extension of the tumor. Next, the planning target volume (PTV) is obtained by expanding the CTV to account for internal target motion and setup uncertainties during treatment as described in more detail below.

Whereas the bones that comprise the pelvic girdle are rigid and fixed, all of the soft tissues, and in particular, the pelvic viscera, may change in size and position over time. The planning CT scan documents the positions of these structures at the time the treatment is planned but not at the time the treatment is delivered as the position may have changed between the time the planning CT is acquired and treatment is delivered. Furthermore, the patient orientation with respect to the radiation beams, as documented by the planning CT, must be reproduced accurately during every treatment session to ensure adequate dosimetric and geometric coverage of the tumor and the exclusion of sensitive anatomy. When the planning CT is acquired, reference marks (tattoos) are placed on the skin of the patient and on any rigid immobilization devices used to reproducibly relocate the patient for daily treatment. These marks define the isocenter within the prostate, and the isocenter, thus defined, must be reproducibly aligned with the isocenter of the linear accelerator for daily treatment. This is typically achieved by aligning a set of three orthogonal lasers to the tattoos and through imaging.

However, neither of these techniques completely eliminates sources of geometric uncertainties in the radiation delivery. As such, they result in inaccuracies in reproducibly delivering EBRT to a targeted isocenter. The approach used to compensate for the lack of geometric precision in isocenter targeting, therefore, is to expand the CTV to arrive at a PTV during treatment planning. The PTV is obtained by adding a setup margin to account for setup uncertainties and an internal margin to the CTV to account for anticipated deviations from the anatomic relationships documented in the planning CT.

In addition to the target volumes, organs at risk (OARs) are also contoured. Dosimetric constraints to these as well as to the target volumes are used as input to an algorithm that optimizes the calculated dose distribution on the CT so that the desired prescribed dose is delivered to the target and the dose to the organs does not exceed the constraints.

In this example, the planning CT, target volumes (GTV, CTV, PTV, OARs), calculated radiation dose distribution, dose calculation algorithms, details about the radiation beams and linear accelerator on which the patient will be treated, plan information in the electronic medical record system and the patient's documentation such as the prescribed radiation dose and fractionation, imaging instructions during treatment, independent verification of the calculated dose, measurement of the deliverability of the planned dose on the treatment machine, special physics consults to address instances where the patient is being retreated, has a pacemaker or a prosthesis, for instance, define the RT chart.

A number of quality assurance checks are performed on the RT chart during the treatment planning process to ensure the safety and efficacy of these complex treatments. The most important, complex and time-consuming of these checks is the pre-treatment physics chart review (TPCR). This check is performed prior to the start of treatment to verify the safety, integrity and consistency of all aspects of the treatment chart from the documentation to the integrity of the CT used for planning, the quality and safety of the planned treatment and the correctness of the transferred plan in the electronic medical record system. Treatment cannot start until this review is complete and the RT chart has been determined to be safe and free of errors. If the treatment plan contains errors and is therefore not approved for treatment, a fail safe interlock on the treatment machine prevents the radiation from being delivered to the patient.

TPCR is typically performed by a medical physicist. The TPCR entails a multi-step verification of the defined treatment. It involves interaction with an inter-disciplinary team consisting of dosimetrists, radiation oncologists and therapists, and a detailed knowledge of multi-vendor software and hardware systems, as shown in FIG. 2. The TPCR can involve the verification of more than 300 variables for completeness, integrity and consistency across multiple software applications and interaction with at least 3 other staff members. The medical physicist is usually expected to perform the TPCR within 30 minutes to one hour and frequently has multiple charts to check simultaneously.

Studies have shown that the treatment planning process is the main source of errors in radiation oncology, thus underscoring the importance of TPCR in detecting errors prior to treatment and ensuring the safety and quality of the treatment [1]. Currently, this verification is mostly performed manually, with only about 4.7% of personnel (American Association of Physicists in Medicine (AAPM) Task Group (TG) No. 275 survey) in radiation oncology using automated methods during the chart review process. A review of pre-treatment level 3 and 4 errors from the incident learning system at the University of Washington indicated that 62% of potentially detectable events were not detected during the TPCR while a review of the Safety in Radiation Oncology (SAFRON) Database indicated that none of potentially detectable events were detected [1]. The conclusion of these studies was that standardization and automation may improve the chart review process.

Current automated chart review tools are similar to checklist solutions [2-4]. They are limited in that they do not provide contextual information about potential errors, the effect of errors on other variables in the chart or the relationship between different errors. They also do not provide information that will assist with error correction such as the location in the treatment chart where all instances of a specific variable appears, the severity of errors and the order in which they should be corrected. Nor do existing solutions dynamically track the solution state of the automated TPCR.

It would be desirable therefore to provide an automated TPCR solution that addresses the above limitations and also verifies and validates the logical consistency and completeness of systems specifications and software implementation. It would be further desirable to provide a system and method for a comprehensive review process that reduces or eliminates human error and prevents a faulty radiation plan from being delivered on the treatment machine. It would be yet further desirable to provide a software-based plan checking system to increase reliability, effectiveness and efficiency of a pre-treatment chart review. As the field moves to further integrate real-time imaging to verify target and soft tissue position during treatment and real-time re-planning of the dose to be delivered to the target, it is desirable to incorporate real-time chart reviews and real-time fail-safe interlocking within these real-time treatment solutions. Such a chart review process will allow real-time adjustment to the treatment, within bounds.

SUMMARY OF THE EMBODIMENTS

In accordance with one embodiment of the invention, computer-implemented method of evaluating a protocol for radiation therapy for a target volume of a patient, the method uses a computer system executing software instructions establishing computer processes. The computer processes include receiving and storing data defining the protocol and characterizing the target volume. The computer processes include parsing the data to extract parameters characterizing the protocol. The computer processes include applying the extracted parameters and the target volume to a model, wherein the model represents relationships among sub-processes and variables pertinent to execution of the protocol in a patient. The computer processes include obtaining from the model an evaluation of the protocol and providing the evaluation as an output.

Optionally, the relationships include dependencies, constraints, and conflicts among the sub-processes and the variables. Optionally, each of the sub-processes includes at least one of the variables. Alternatively or additionally, the sub-processes represent at least three members selected from the group consisting of dose prescription, documentation verification, planning CT integrity, anatomical contours, beam configuration, dose calculation, treatment plan parameters, dose volume histogram, 3D dose distribution, intensity modulated radiation therapy (IMRT) quality assurance, monitor unit (MU) check, treatment setup and imaging instructions, treatment approval, and combinations thereof. Alternatively or additionally, each sub-process interfaces with at least one module, wherein each module is a database system having data for a subset of the variables, and is automatically queried to retrieve data for at least one variable included in the sub-process. Alternatively or additionally, at least one module includes a documentation module, a treatment planning system, a patient-specific QA database, an electronic medical records database, and an MU check database.

Optionally, the variables represent at least three members selected from the group consisting of prescribed dosage, number of fractions, dose to gross tumor volume, dose rate, treatment modality, planning target volume, beam energy, dose calculation algorithm, plan status, and combinations thereof. Optionally, the computer processes further comprise building the model by decomposing a TPCR process specification into the sub-processes, the variables, and modules. Alternatively or additionally, the computer processes further comprise preparing the model for performing evaluations on the protocol, including formalizing the model by converting it into a series of equations, and performing verification on the model by solving the series of equations using constraint programming. Alternatively or additionally, the computer processes further comprise applying sample protocols for radiation therapy to the model using constraint programming to determine the model's validity.

Optionally, the parameters of the protocol are automatically retrieved by querying one or more modules based on identity of the patient. Optionally, applying the extracted parameters and the target volume to the model includes, for each sub-process, checking a subset of the parameters against corresponding variables in the sub-process to determine conflicts pertinent to the subset of parameters. Alternatively or additionally, checking the subset of the parameters includes determining an optimal order and priority for the checking. Alternatively or additionally, checking the set of the parameters is performed according to a member of the group consisting of: continuously, in real-time, while formulating the protocol for radiation therapy, on the protocol after formulation of the protocol is complete, and combinations thereof. Alternatively or additionally, when the method is performed on the protocol after formulation, applying the extracted parameters and the target volume to the model is performed, with respect to each sub-process, either simultaneously or sequentially. Alternatively or additionally, checking the subset of the parameters includes determining whether each parameter causes a conflict with a value set for any of the other extracted parameters.

Alternatively or additionally, checking the subset of the parameters includes: for each parameter of the subset, determining a severity of the conflict based on a pre-defined score assigned to a variable corresponding to the parameter, and causing graphical display of the subset of parameters and the corresponding severities for analysis. Alternatively or additionally, determining (i) a set of source variables that are a cause of the conflict, and (ii) a set of propagation variables that are affected by the conflict, and causing graphical display of (i) the set of source variables and (ii) the set of propagation variables for analysis. Alternatively or additionally, checking the subset of the parameters further includes: modeling the relationships among the variables in a directed graph, such that the directed graph represents, for each variable, other variables that influence the variable and other variables that are influenced by the variable, determining a variable associated with a given parameter of the subset of parameters, and analyzing relationship of the determined variable in the directed graph to locate (i) the source variables which influence the variable, and (ii) the propagation variables that are influenced by the variable. Optionally, checking the subset of the parameters includes tracking the evaluation of the protocol by assigning states to the sub-processes and variables.

BRIEF DESCRIPTION OF THE DRAWINGS

The foregoing features of embodiments will be more readily understood by reference to the following detailed description, taken with reference to the accompanying drawings, in which:

FIGS. 15A-15B illustrates automated chart review reports generated from evaluating a patient's treatment protocol in accordance with an embodiment of the present invention.

DETAILED DESCRIPTION OF SPECIFIC EMBODIMENTS

Figure 1:
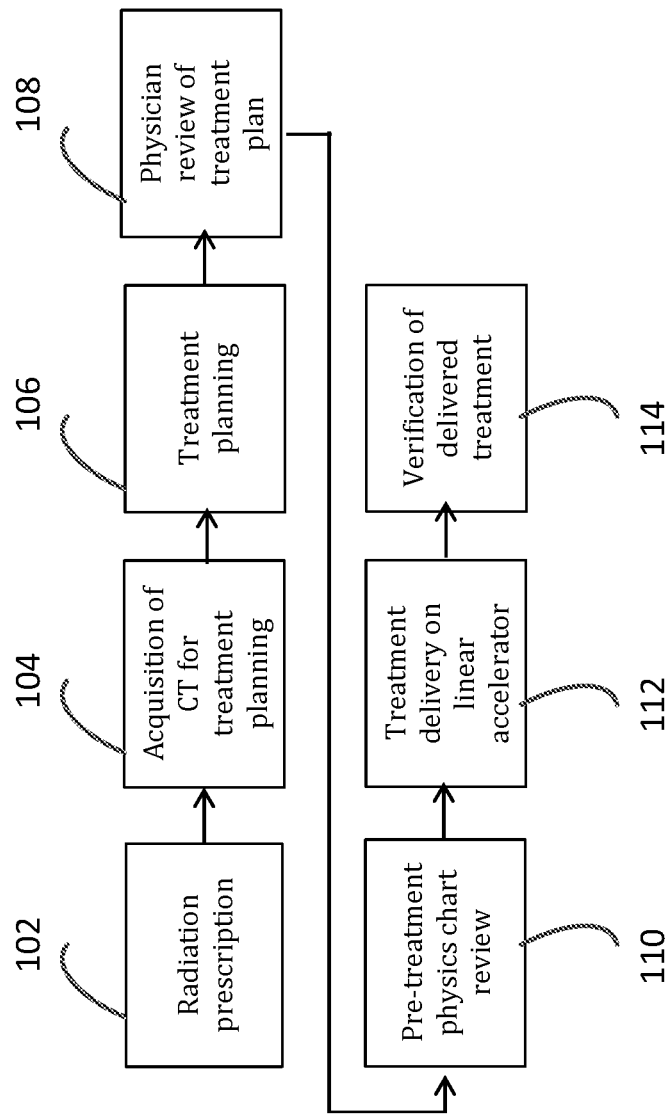
FIG. 1 illustrates the customary steps in radiation therapy planning and delivery.

Definitions. As used in this description and the accompanying claims, the following terms shall have the meanings indicated, unless the context otherwise requires:

A "computer process" is the performance of a described function in a computer using computer hardware (such as a processor, field-programmable gate array or other electronic combinatorial logic, or similar device), which may be operating under control of software or firmware or a combination of any of these or operating outside control of any of the foregoing. All or part of the described function may be performed by active or passive electronic components, such as transistors or resistors. In using the term "computer process" we do not necessarily require a schedulable entity, or operation of a computer program or a part thereof, although, in some embodiments, a computer process may be implemented by such a schedulable entity, or operation of a computer program or a part thereof. Furthermore, unless the context otherwise requires, a "process" may be implemented using more than one processor or more than one (single- or multi-processor) computer.

A "sub-process" is a "computer process". "Sub-processes" include the variables of patient treatment plans (e.g., RT charts), grouped by functionality and location with the plan, and the series of checks to be performed on these variables.

A "set" includes at least one member.

A "target volume" of a patient is a specific volume of the patient having properties not just of a volume in general but rather of the patient in particular.

"Modules" are the different software systems containing information about patient treatment plans, such as an RT chart.

"Variables" are representations of the items being checked in a patient treatment plan, such as an RT chart.

An "independent variable" informs or influences, directly or indirectly, a dependent variable. Usually, the independent variable precedes the dependent variable in time either in the order in which it is entered or generated in the treatment chart or in the order in which it is checked.

A "dependent variable" is a variable we are trying to explain while an independent variable is the variable that "explains" the dependent variable. Dependencies can be linear or circular. A circular dependency means that the variables are mutually dependent on each other.

A "conflict" exists between two variables when the value taken by one variable precludes a value taken by the second variable.

"Dependencies among sub-processes" determine the order in which the sub-processes are visited.

Disclosed herein are embodiments of a computer-implemented method for reducing error and increasing efficacy in quality assurance (QA) and clinical workflow processes in radiation oncology. These embodiments address the pre-treatment physics chart review (TPCR) using methods to dynamically track the state of process variables in a patient's treatment chart and automatically identify logical inconsistencies between variables, the severity of these inconsistencies, the context in which these inconsistencies arise, and how the inconsistencies propagate.

The treatment of patients with radiation therapy requires the development and evaluation of a detailed patient-specific treatment plan to deliver radiation to the tumor. Without a specific treatment plan, significant errors may arise in the delivery of radiation, which may result in serious consequences.

It has been shown that most errors in radiation therapy arise in the treatment planning process. This underscores a need for appropriate safety checks to detect and prevent these errors. Quality assurance in radiation oncology entails a multi-step verification of these complex, high technology treatments. It involves interactions with an inter-disciplinary team and a detailed knowledge of multi-vendor software and hardware solutions. Due to the high volume of patients scheduled to start their radiation therapy treatment on any given day, often multiple treatment charts need to be verified concurrently. Currently, this verification is performed manually.

Disclosed herein are embodiments of a novel method for providing an improved quality assurance process as a solution that reduces the number of steps and time for verification of a patient's treatment chart and reduces error rates that exist in current manual processes. The embodiments build knowledge about system behavior into the QA process. Some embodiments decompose these QA processes into a model of tractable units (e.g., sub-processes, modules, and variables), and include in the model dependencies and conflicts between variables in the patients' treatment charts. These embodiments prepare checks to be performed on the variables, in the context of the sub-processes and modules, to ensure the variables conform to the system requirement specifications. During execution of these checks, these embodiments dynamically track the state of the variables to automatically identify logical inconsistencies (potential errors) in the treatment charts, severity of the inconsistencies, their source, and how the inconsistencies propagate.

This information is important in helping the chart reviewer evaluate the consequences of the errors, prioritize risk to the patient, and prioritize the order in which errors need to be corrected. A patient's treatment chart and radiation treatment plan can only be approved for treatment and, therefore delivered for use on the treatment machines, if free of errors. If any errors are present at this stage of the QA process, the patient's treatment cannot proceed and a safety interlock on the treatment machine prevents the prescribed radiation from being delivered.

Furthermore, disclosed herein are embodiments of a method for verifying the logical correctness and completeness of the specifications and software implementation in the improved QA process using techniques from computer-aided verification. The formalization and automation of these QA processes is expected to lead to improved patient safety and increased clinical efficiency in terms of increased correctness of the treatment plan, reduced delays in patient treatments and reduced effort and time for performing this important task.

Overview of Embodiments

The pre-treatment physics chart review is designed to identify and address errors and inconsistencies in the treatment plan prior to treatment. It ensures the quality and safety of the patient's treatment plan. The identification and resolution of such issues prior to treatment also helps reduce delays during the patient's treatment and improve clinical efficiency. The TPCR is performed manually by a medical physicist. While the chart review process can be different at different institutions it is similar in its main aspects. The TPCR is expected to become more standardized with the release of the AAPM Task Group No. 275 report (Strategies for Effective Physics Plan and Chart Review in Radiation Therapy, TG275).

Embodiments of the present invention use techniques from computer science to assist in the reduction of errors and automation of the pre-treatment chart review process. In accordance with an embodiment, an inventive method lies in an integration of methodology from radiation oncology, medical physics and computer science to decompose the process into tractable units, formalize the problem of determining errors in a patient's treatment plan or protocol, dynamically track the solution state and automatically identify errors, their source, their severity in terms of potential to cause harm to a patient and their impact on other variables in the treatment chart in terms of how the errors propagate. Such a comprehensive solution does not currently exist.

In embodiments, the use of formal verification methods (methods from Computer Aided verification) for independent verification and validation of software specifications of a large, safety critical and complex software system to ensure that the specifications are consistent and complete and can be met by treatment plans or protocols. It is also important to validate the formalization and implementation to ensure that the system conforms to the specifications. Through such introduced formalization, embodiments bring these verification and validation methods to bear on the TPCR. Such formalization and automation of the review process is expected to lead to improved patient safety, reduced patient delays and increased clinical efficiency.

In embodiments, a modular approach was used to decompose the TPCR process into tractable units comprising sub-processes, modules and variables. In these embodiments, module-associated variables served as inputs to the sub-processes, and modules comprise the different software systems containing information about the RT chart and include the treatment planning system, the documents module, independent monitor unit check and the electronic medical record (record and verify) system. In these embodiments, sub-processes describe the variables, grouped by functionality and location within the RT chart and TCPR, and the series of checks to be performed on these variables. A variable belongs to a sub-process if it is entered or generated during the treatment planning process in that sub-process. In these embodiments, sub-processes may include dose prescription, documents, CT integrity, anatomical contours, beam configuration, dose calculation, 3D dose distribution quality, intensity modulated radiation therapy (IMRT) measurement, record and verify and treatment plan approval.

Figure 14A:
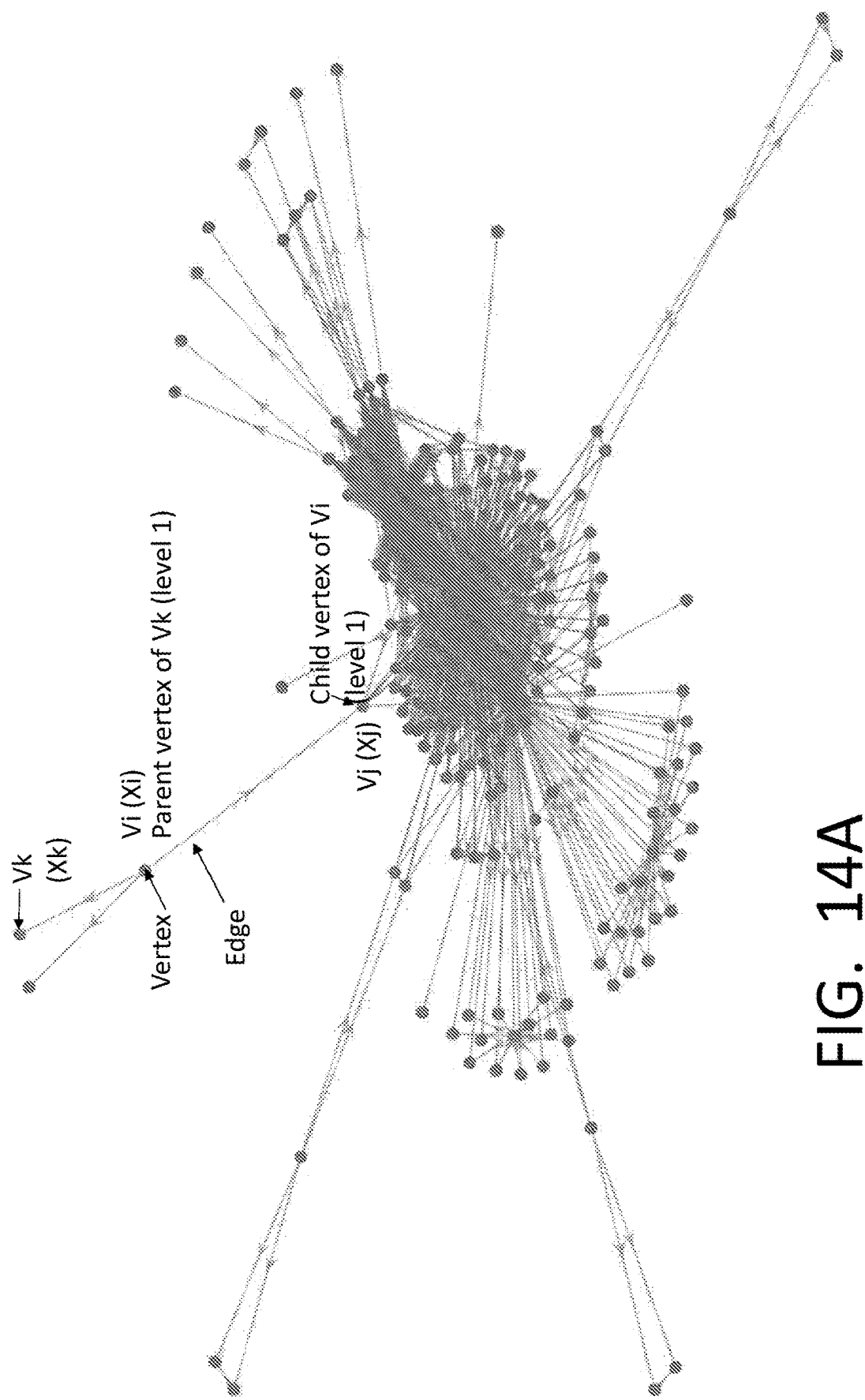
FIGS. 14A-14B are a directed graph and a sub-graph of dependencies with a model of a TPCR process in accordance with an embodiment of the present invention.

In embodiments, dependencies and conflicts between variables are captured in an adjacency matrix, which is then converted into a directed graph (as shown in FIG. 14A). In embodiments, the severity of a logical inconsistency or potential error is defined by a pre-assigned score while the impact of a potential error, or how it propagates, is determined from the connectivity of the inconsistent variable to other variables in the RT chart. In embodiments, the solution state is tracked by assigning states to the variables and sub processes.

In example embodiments, the variables to be checked can be obtained automatically by the chart review program by querying the underlying databases associated with the different software system or from DICOM-RT files.

The solution provided in embodiments of the present invention allows all variables to be checked simultaneously or sequentially, as is the norm. If sequential, in embodiments, the checks performed and sequence in which sub-processes and variables are visited are described in a flowchart representing the order in which the sub-processes are traversed and an activity workflow table. The flowchart also describes the order in which errors can be corrected.

If checked simultaneously, in embodiments, the automated chart review solution presents the user with a dashboard showing all sub-processes and all variables in a single view and allows the correction of conflicting values in a different order from the conventional sequential order. This includes correcting conflicts (inconsistencies) based on an optimal path determined by the solution which results in the least number of revisions to be made. This also includes correcting conflicts based on their connectivity to other variables in the RT chart. This may result, for example, in conflicted variables with the most dependencies or generations of propagation (also called children) variables being corrected first. This path through the solution space allows a more efficient conflict resolution process as the logical inconsistencies or errors that affect the largest number of variables downstream can be corrected first. In contrast, when the user follows a sequential path through the solution space this may be a slower process.

The simultaneous check of all variables capability is useful when the quality assurance of the RT chart needs to be performed in real time. This would be performed, for example at the treatment console on the linear accelerator, during adaptive radiation therapy (ART). On-line ART, which is currently where the field is moving towards, allows for adjustments to the radiation treatment plan during a particular treatment fraction in real time. A comprehensive real time solution for the TPCR, as presented here, would greatly facilitate on-line ART.

Formalization of TPCR Process

Embodiments formalize the TPCR process in order to verify and validate the TCPR process specifications and implementation. Embodiments define a modular solution that:

Decomposes the TCPR process into sub-processes, modules and variables,

Builds information about the behavior of the system to be checked into the solution by modeling the dependencies between both variables and sub-processes including mutual dependencies as a directed graph as well as the variable types constraints and their accepted values with respect to each other. The solution also models conflicts between variables and variables that can be checked in parallel, Models the order and priority of the checks to be performed, if performing sequential checks, in addition to providing the option to perform all checks simultaneously, if desired, Dynamically keeps track of the solution state by assigning states to the variables and sub processes, Formalizes the TPCR process including all variables, dependencies, variable states and types and sub-processes, Verifies and validates the integrity, logical consistency, completeness and satisfiability of the TCPR specifications and software implementation using concepts from formal computer aided verification including constraint programmers and automated model checkers, Verifies the integrity and logical consistency of a proposed treatment plan against the TCPR specification, Automatically detects logical inconsistencies or potential errors in the proposed treatment plan, their source, severity and how they propagate, Finds the optimal path through the variables to be checked so as to minimize the total number of checks and stop-start cycles, including if a variable is changed, while covering all variables, Automatically queries the documents, treatment planning system and record and verify systems from multiple software vendors to automatically check the treatment charts, and Provides feedback to the user regarding the inconsistencies detected, their location in the RT chart and TPCR process, and solution required.

In an example embodiment, the full model for the TPCR process comprised 4 modules, 19 sub-processes and 337 variables (75 distinct) and 1752 dependencies.

After formulating the specifications for the TCPR process system requirements and formalizing the latter, embodiments identify complete paths through all the variables with a minimal number of dependencies, conflicts and stop-start cycles using graph theory. The embodiments are able to automatically identify all variable inconsistencies early and verify how changes to one or more variables affected different stages of the process using the directed graph obtained from the adjacency matrix.

The determination of complete paths allows the following. First, a finite state system can be determined where the next step after each variable is evaluated based on the accumulated histories of previous usage of the solution. This allows analysis-guided capability including a machine learning-guided capability in the use of the automated chart review and in correcting errors based on previous successful stage. A probability can be assigned to the next step resulting in a stochastic process.

In embodiments, the solution that has been developed can be used in a real-time manner during or after treatment planning. During treatment planning or after the treatment chart is completed. In these embodiments, when used during treatment planning it runs in the background to provide assistance to a user who is performing the TCPR. In embodiments, as the user completes each step of the TCPR the solution informs the user of the status of the chart check, how many variables, modules, sub-processes have been completed and how many remain and if any logical inconsistencies exist in the developing solution, and how the inconsistencies can be avoided.

Definition of Modules, Sub-processes, Variables, Dependencies, Conflicts, Constraints and Dynamic Tracking of Solution State The key aspects of the solution in embodiments of the present invention are listed below.
- The dependencies and conflicts between all variables in the TCPR process was captured in an adjacency matrix which was then converted to a directed graph,
- All variables, their types, their permissible values individually or with respect to other variables, the modules to which they belonged and the sub-processes to which they served as input were accurately documented,
- The checks performed and sequence in which sub-processes and variables were visited was described in a flowchart and an activity workflow table,
- The solution state was tracked by assigning states to the variables and sub-processes, and
- The severity of a logical inconsistency or error was determined from a preassigned score and the impact of their impact on other variables was determined from the connectivity of the variable.

Formal Specification, Verification and Validation

Embodiments formalize the above using techniques from computer-aided verification including constraint programming and automated model checking. The formalization allows us to mathematically verify and validate the logical consistency and completeness of the above specifications and implementation of the checks. The embodiments can automatically detect if variables in the treatment chart are inconsistent with the permissible values they can take by themselves or with respect to other variables and provide feedback to the user regarding the nature of the inconsistencies on test examples designed to test for inconsistencies in the dose prescription, treatment modality, independent checks of the plan and dose distribution.

Iterative Solution with Feedback

An automated solution to the TCPR process can be obtained by iterating through the following steps until the entire TCPR process is modelled:
1. Specification of part of the TCPR process, variables including types and allowed values, modules, sub-processes, checks to be performed, priority and importance of checks and the variable states while the checks are being performed,
2. Formalization of the specifications of the TCPR process,
3. Formal verification of the TCPR process,
4. Validation of the formalization by testing for the detectability of known errors and inconsistencies,
5. Software implementation of a prototype,
6. Verification and validation of the prototype,
7. Refinement and increase in scope of the model and prototype Embodiments of the present invention formalized and validated the TCPR process and automatically detected inconsistencies in patient treatment charts. Such formalization and automation helps improve patient safety and clinical efficiency by reducing our reliance on time-consuming and error-prone manual checks. Our approach shows the need to integrate methods from medical physics, radiation oncology and computer science in order to obtain a solution that is logically correct and consistent, complete and informative to the user. The methods proposed here can be extended to other areas in radiation oncology such as the automation of clinical workflows and patient care paths. Being modular, the solutions proposed can also be adapted for different TPCR processes in different clinics.

Drawings

FIG. 1 illustrates the customary steps in radiation therapy planning and delivery. Prior to commencing radiation treatment, the patient's physician enters a prescription for the radiation dose to be delivered to the patient 102. In order to create the patient-specific, prescribed radiation treatment plan, a 3D diagnostic energy (kilovoltage) CT scan of the patient's pelvis is then acquired for treatment planning purposes 104. The planning CT gives accurate three-dimensional anatomical information about the patient's bony and soft tissue anatomy, enabling delineation of the gross tumor volume, clinical target volume, planning target volume and other anatomically relevant organs and structures. Dosimetric constraints to these as well as to the target volumes are used as input to an algorithm that optimizes the calculated dose distribution on the CT so that the desired prescribed dose is delivered to the target and the dose to the organs does not exceed the constraints 106. The planned treatment is then reviewed for correctness by a physician (radiation oncologist) 108. After the physician has reviewed the planned treatment, a medical physicist performs the pre-treatment physics chart review. This check is performed prior to the start of treatment to verify the safety, consistency and integrity of all aspects of the treatment chart from the documentation to the integrity of the CT used for planning, the quality and safety of the planned radiation dose distribution and the correctness of the transferred plan in the electronic medical record system. If no errors are detected in the treatment chart, the treatment plan is approved for treatment by the medical physicist 110. The planned treatment is delivered to the patient on the treatment machine 112. Additional checks are performed to verify the correctness of the delivered dose 114. While this example illustrates the use of a linear accelerator it is more generally applicable for other types of treatment machines.

Figure 2:
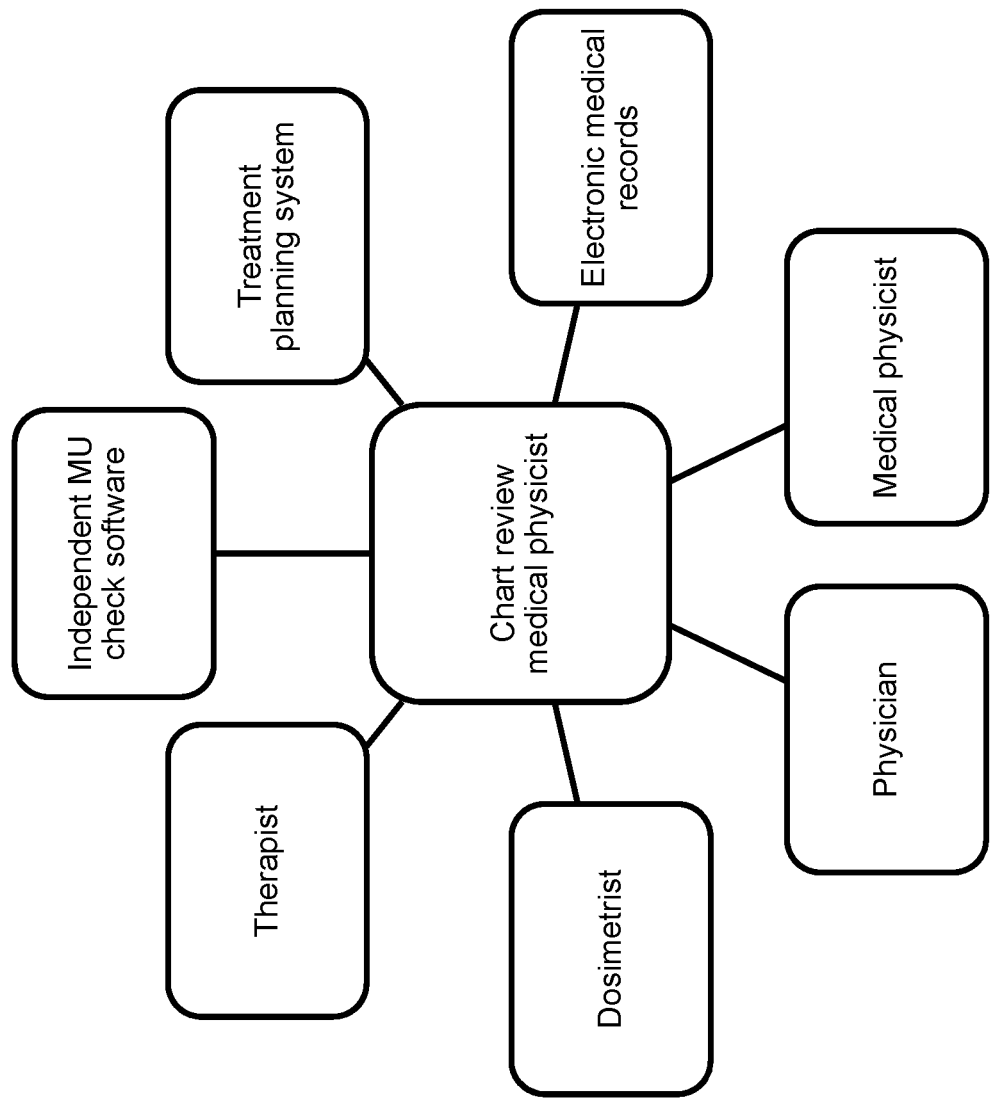
FIG. 2 illustrates interactions in a TPCR process, which is commonly performed on a patient's RT chart.

FIG. 2 illustrates interactions in a TPCR process, which are commonly performed on a patient's RT chart. The TPCR is typically performed by a medical physicist and entails a multi-step verification of the defined radiation treatment plan. It involves interaction with an inter-disciplinary team consisting of dosimetrists, radiation oncologists, therapists and other medical physicists, and a detailed knowledge of multi-vendor hardware and software systems including the treatment planning system, electronic medical records interface and independent monitor unit calculation software.

Figure 3A:
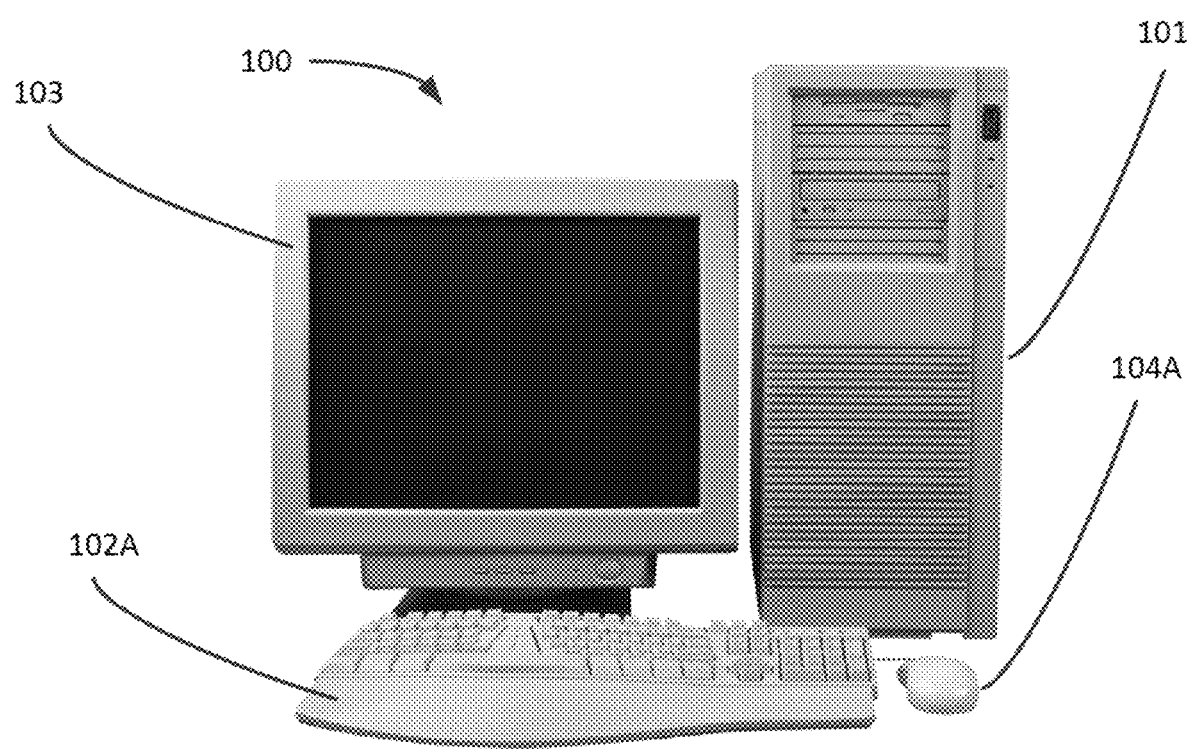
FIG. 3A illustrates a typical computer that can be configured to implement some or all of an evaluation system in accordance with an embodiment of the present invention.

FIG. 3A illustrates a typical computer that can be configured to implement some or all of an evaluation system and methods in accordance with an embodiment of the present invention.

The computer 100 includes a central processing unit (CPU) 101, a keyboard 102A, a monitor or display device 103, and a conventional mouse 104A or other pointing device. The computer may be a desktop computer, laptop, tablet, mobile device (e.g., smartphone), etc. The CPU 101 may include both dynamic memory and static memory, such as a hard disk drive. The CPU also includes a microprocessor in communication with the memory, and is configured to execute instructions stored in the memory. To that end, the memory, the disk drive, or both, may be configured to be non-transient and to store executable computer instructions indefinitely. The instructions, when executed by the microprocessor, may implement some or all of the operations and processes described herein to evaluate a treatment plan of a patient. Steps of the evaluation methods, in embodiments of the present invention, are presented to a user (e.g., a doctor, clinical technician, etc.) through a graphical user interface displayed via the display device 103, and the user may interact with the graphical user interface to provide input to these methods. The output of the steps may also be presented to the user through the graphical user interface.

The CPU may also include a communications interface, such as a modem or Ethernet port, configured to send emails, SMS messages, or to communicate with other systems, directly or via a network, to execute the operations and actions described herein. Such a system 150 is schematically illustrated in FIG. 3B.

Figure 3B:
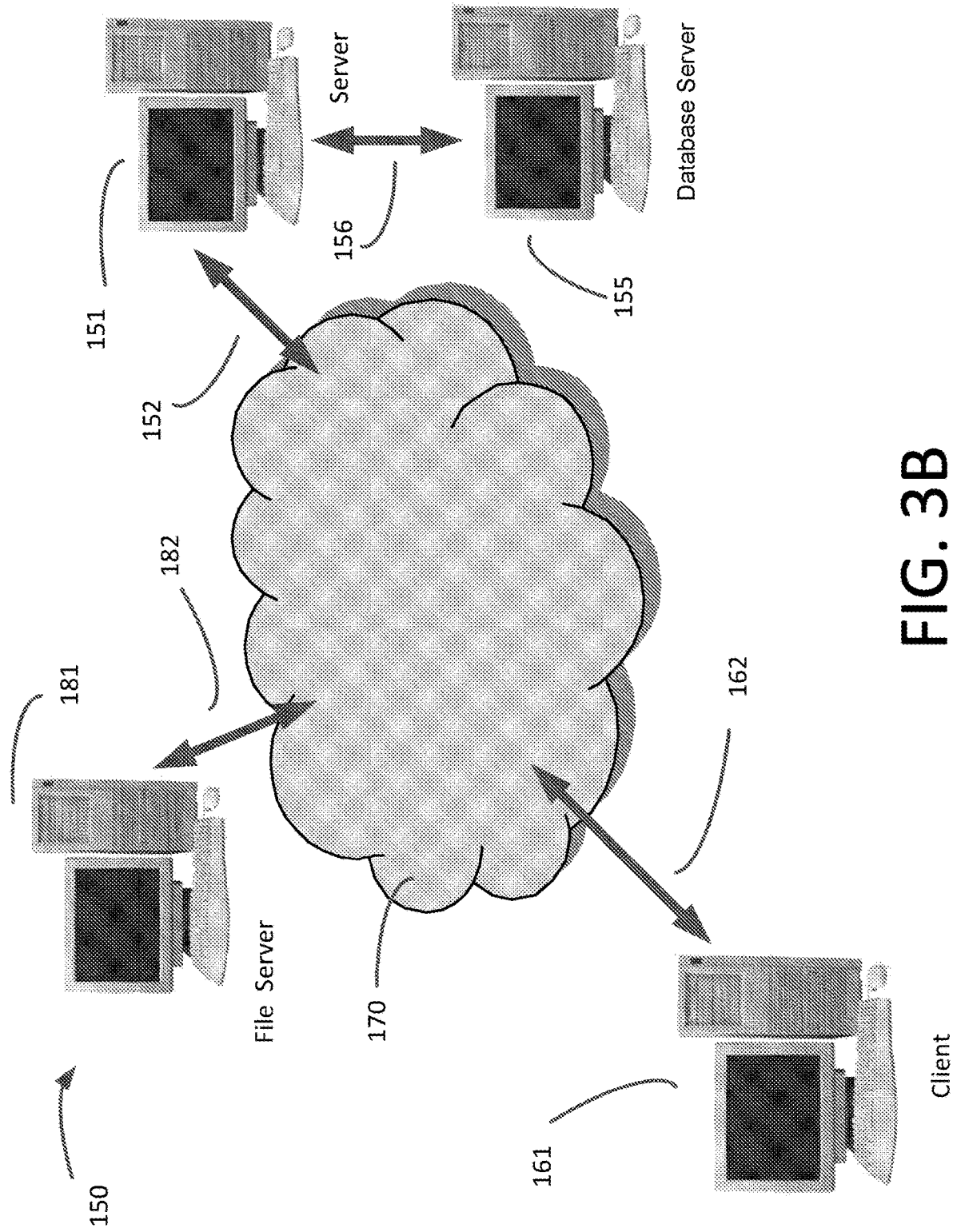
FIG. 3B illustrates a network of computers, similar to the computer of FIG. 3A, that can be configured to implement some or all of a corresponding network-based evaluation system in accordance with an embodiment of the present invention.

FIG. 3B illustrates a network of computers, similar to the computer of FIG. 3A, that can be configured to implement some or all of a corresponding network-based evaluation system and methods in accordance with an embodiment of the present invention. In FIG. 3B, the evaluation system and methods are implemented at least in part on a server computer 151, a database server 155, and a file server 181. A user may interface with the evaluation system and methods executing on the server computer 151 from a remote terminal (e.g., a "client") 161 over a communications link 170. Any of the computers 151, 155, 161, 181, may be a computer such as computer 100, for example. The communications link 170 may be a local area network, or the Internet, to name two examples. The server 151, remote terminal 161, and file server 181 may each communicate to and through the communications link 170 by establishing a communications connection (152, 162, and 182, respectively) with the communication link 170 via their respective communications interfaces. The server 151 may also communicate with a database server 155 via a communications link 156.

Figure 4:
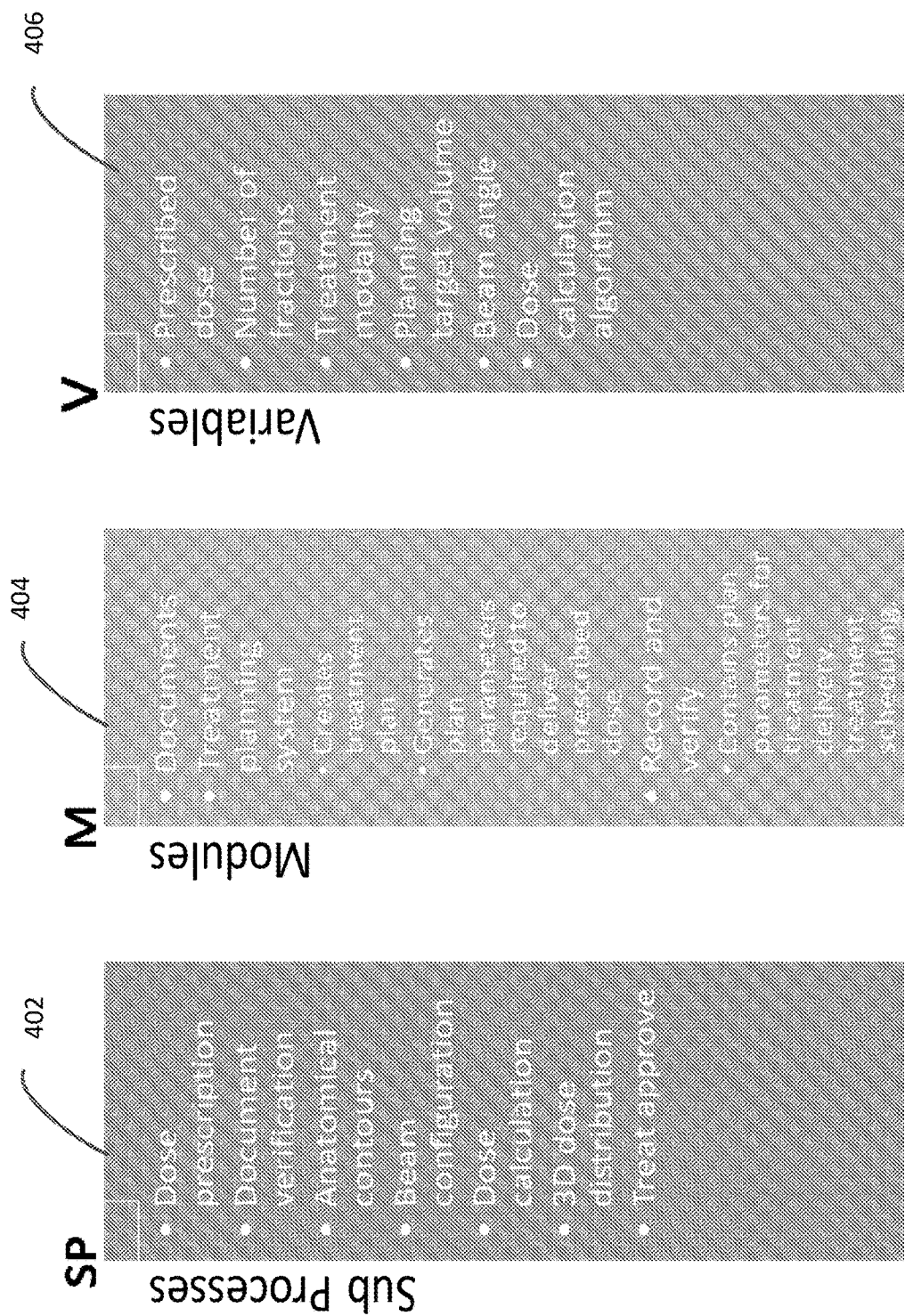
FIG. 4 illustrates example components in which a TPCR process is decomposed in accordance with an embodiment of the present invention.

FIG. 4 illustrates example components in which a TPCR process is decomposed in accordance with an embodiment of the present invention.

Embodiments of the present invention provide a modular approach in which TPCR process specifications are decomposed into a model of tractable units, including the sub-processes 402, the modules 404, and the variables 406, as shown in FIG. 4. The model is executed by a chart review program running on the computer 100 of FIG. 3A, or the client 161 or severs 151 of FIG. 3B. During the TPCR, different activities are performed to verify the treatments for patients (in the patients' charts, such as RT charts in the case of radiation therapy). These activities include dose prescription, documentation verification, CT integrity, anatomical contours, beam configuration, dose calculation, 3D dose distribution quality, intensity modulated radiation therapy (IMRT) measurement, record and verify, treatment plan approval, etc. Each such activity is represented in the model as one or more of the sub-processes 402. Each sub-process 402 includes: (i) the variables 406 of the chart (treatment plan) associated with a particular activity, grouped by functionality and location within the chart or TPCR process specification, and (ii) at least one series of checks to be performed on these variables. A variable 406 is associated with a given sub-process if it is entered or generated during the treatment planning process as part of the activity represented by the given sub-process. The variable 406, such as prescribed dose, number of fractions, treatment modality, planning target volume, beam energy, and dose calculation algorithm, is a representation of the items being verified in the chart for the associated sub-system 402. Appendix A illustrates an example list of sub-processes 402 and their associated variables 406. Appendix B illustrates the series of checks performed by sub-systems on their associated variables.

The model also captures relationships with respect to the variables and the sub-processes, such as dependencies (including mutual dependencies), conflicts, constraints on variable type and accepted values. By such modeling, information about the behavior to be checked is built into the model used to perform the checks on the variables. These dependencies, constraints, and conflicts may be captured using an adjacency matrix, which may then be converted into a directed graph for analysis.

Figure 5:
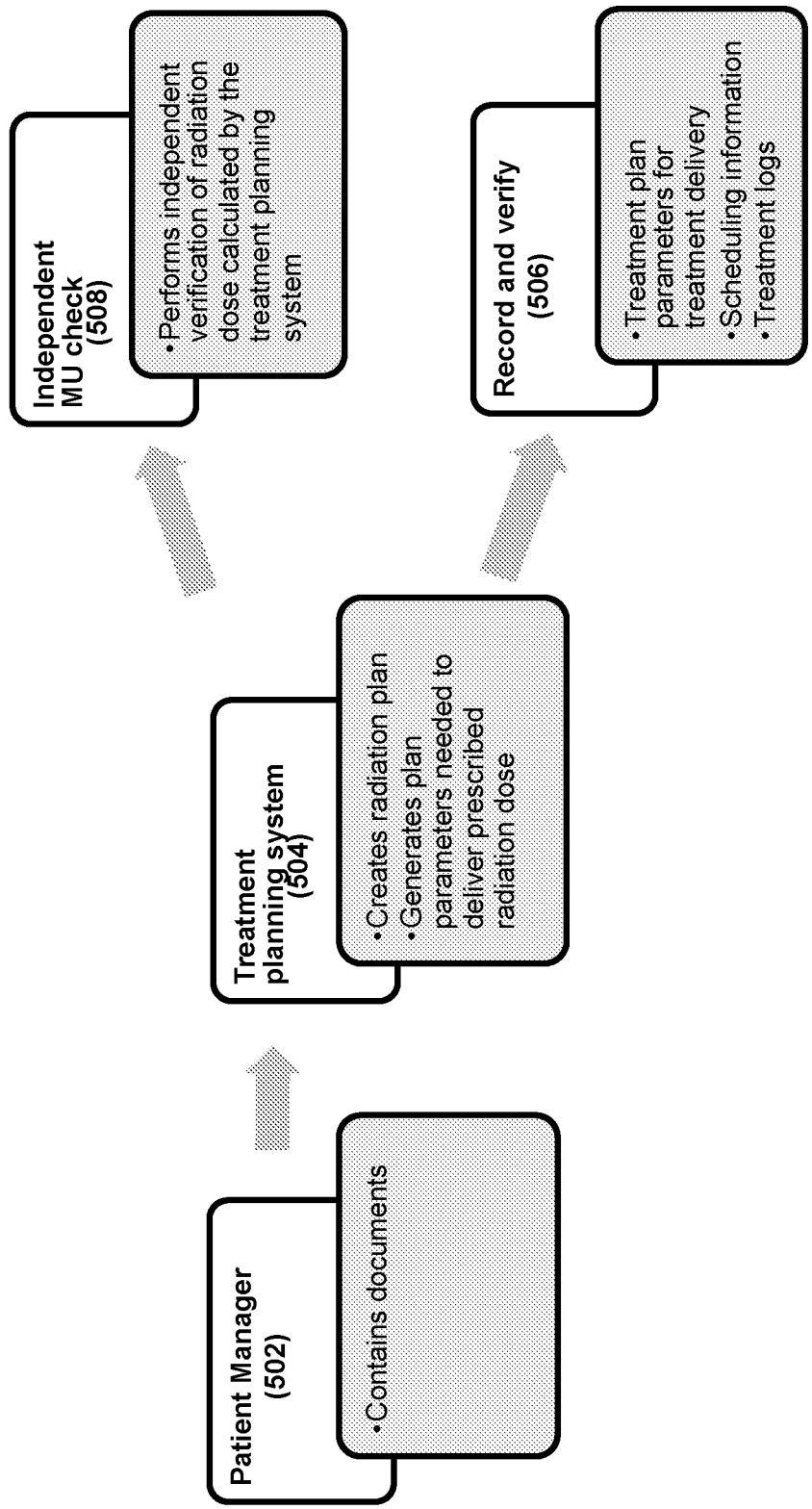
FIG. 5 illustrates the logic flow data among the module components of the decomposed TPCR process in accordance with an embodiment of the present invention.

To obtain the variables in a sub-process, the chart review program interfaces with modules 404 that represent the different software systems having databases containing variable data associated with patient treatment plans. The obtained module-associated variables serve as inputs to the sub-process. FIG. 5 illustrates the logic flow of data among four modules 404 in accordance with embodiments of the present invention. The four modules include a documents module (or patient manager) 502, which contains documents; a treatment planning system 504, which creates a radiation plan, generates plan parameters needed to deliver prescribed radiation dose; an independent monitor unit (MU) check system 508, and an electronic medical record (record and verification) system 506, which contains treatment plan parameters for treatment delivery, scheduling information, and treatment logs, etc.

Figure 6:
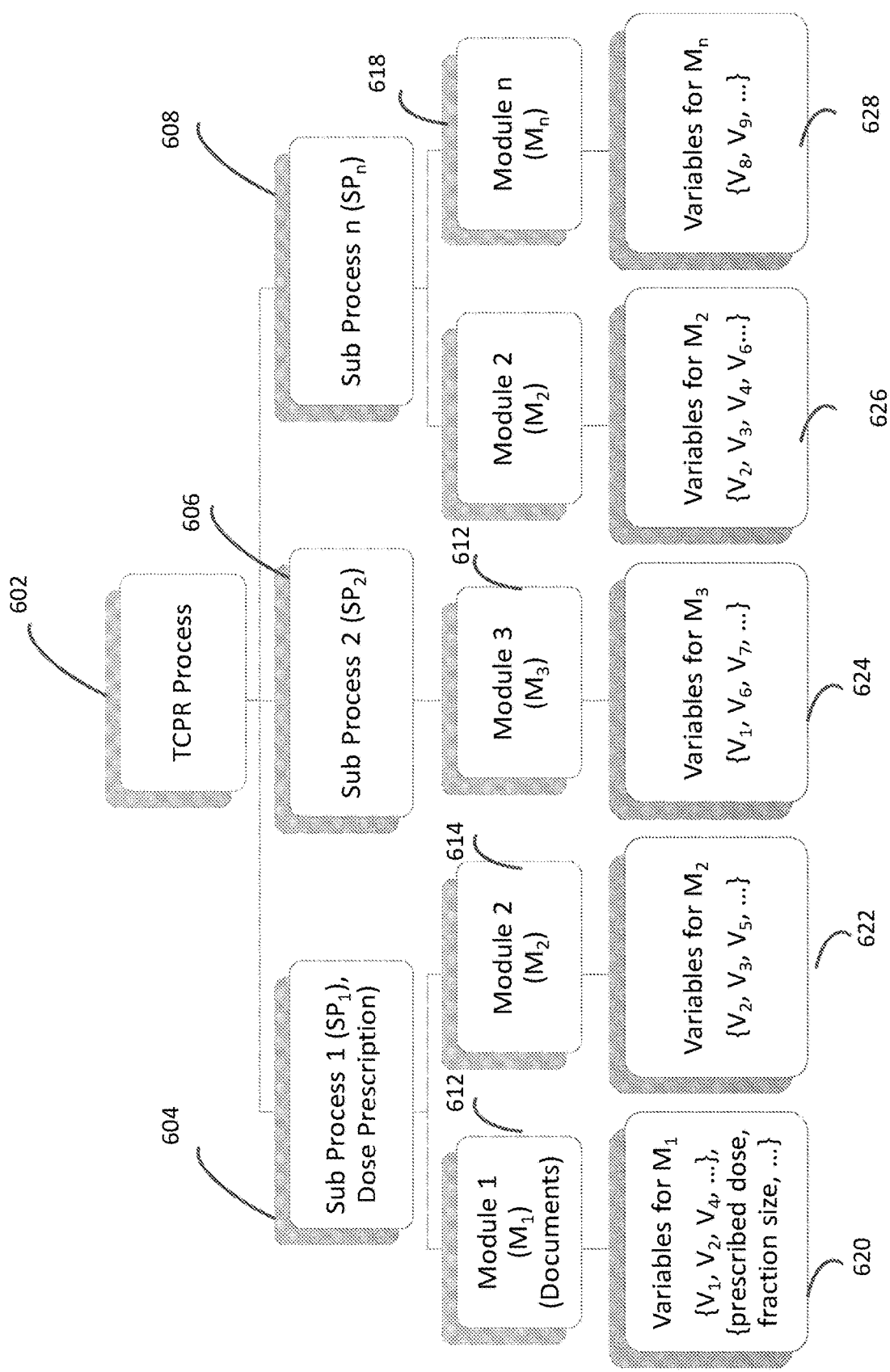
FIG. 6 illustrate a hierarchical structuring of a decomposed TPCR process in accordance with an embodiment of the present invention.

FIG. 6 illustrates the hierarchical structuring of a decomposed TPCR process 602 specification in accordance with an embodiment of the present invention. As shown in FIG. 6, the TPCR process is decomposed in N-sub-processes 604, 606, . . . , 608 that each represent an activity performed to formulate the treatment for a patient. For example, Sub-Process 1 604 represents dose prescription. Each sub-process interfaces with one or more corresponding modules 610, 612, 614, 618 through a chart review program. Different sub-processes may interface with the same module, for example, in FIG. 6, both Sub-process 1 604 and Sub-process N 608 interface with Module 2 612. Each module stores a set of variables 620, 622, 624, 626, 628 in its associated database. For example, Module 1 612 stores variables {V1, V2, V4, . . . } 620, which correspond to {prescribed dose, fraction size, etc). Through the interface with Module 1 612, Sub-process 1 604 obtains this set of stored variables 620 for executing an evaluation of the dose prescription part of the treatment plan.

Figure 7:
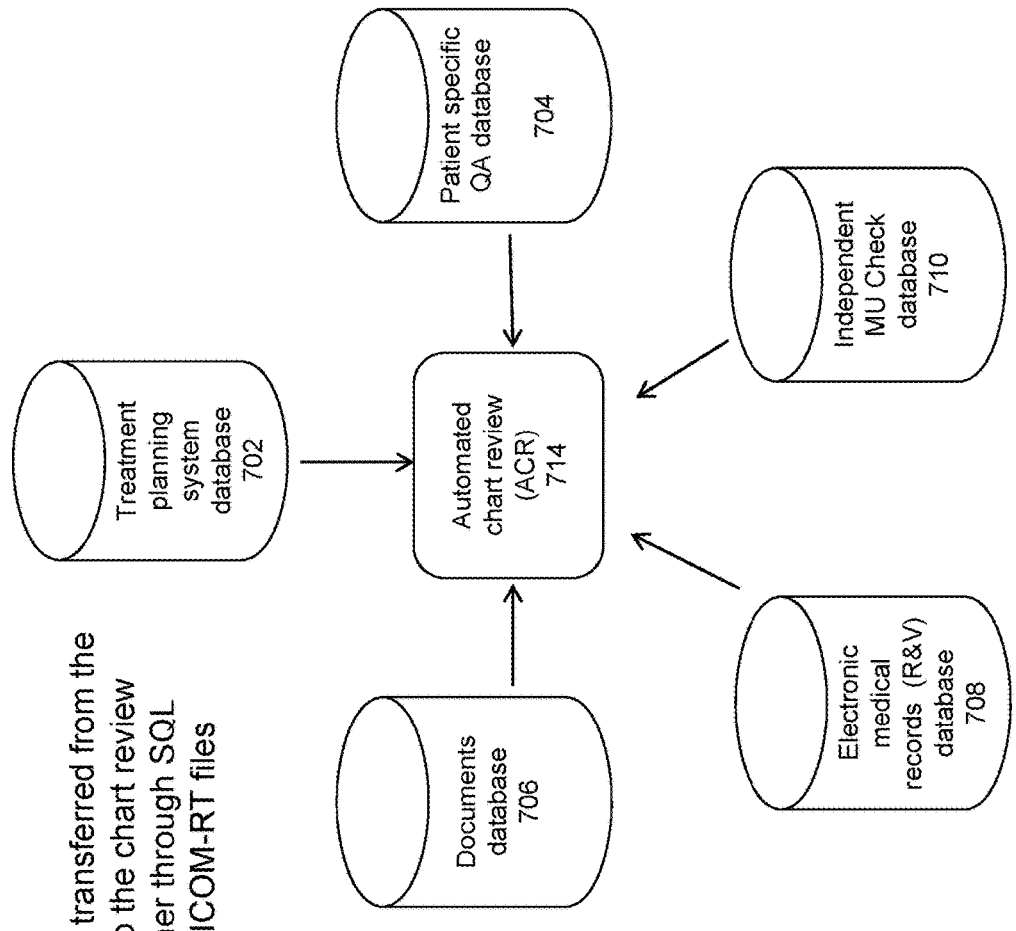
FIG. 7 illustrates example module databases used to access data associated with variables of a patient's chart in accordance with an embodiment of the present invention.

FIG. 7 illustrates an example database structure used by example methods to accesses data associated with variables of a patient's chart in accordance with an embodiment of the present invention. FIG. 7 shows the databases (treatment planning system database 702, patient specific QA database 704, documents database 706, electronic medical records (record and verify) database 708, and independent MU check database 710) corresponding to the modules 404. FIG. 7 further shows that the chart review program 714 obtains variables for a given sub-process from the databases 702, 704, 706, 708, 710 through SQL querying or DICOM-RT file.

The model also represents the order and priority of checks to be performed on the variables for errors, in addition to providing the option to perform all checks simultaneously. During execution of an evaluation method, the model dynamically keeps track of the test state by assigning states to the variables and sub-processes.

Figure 8:
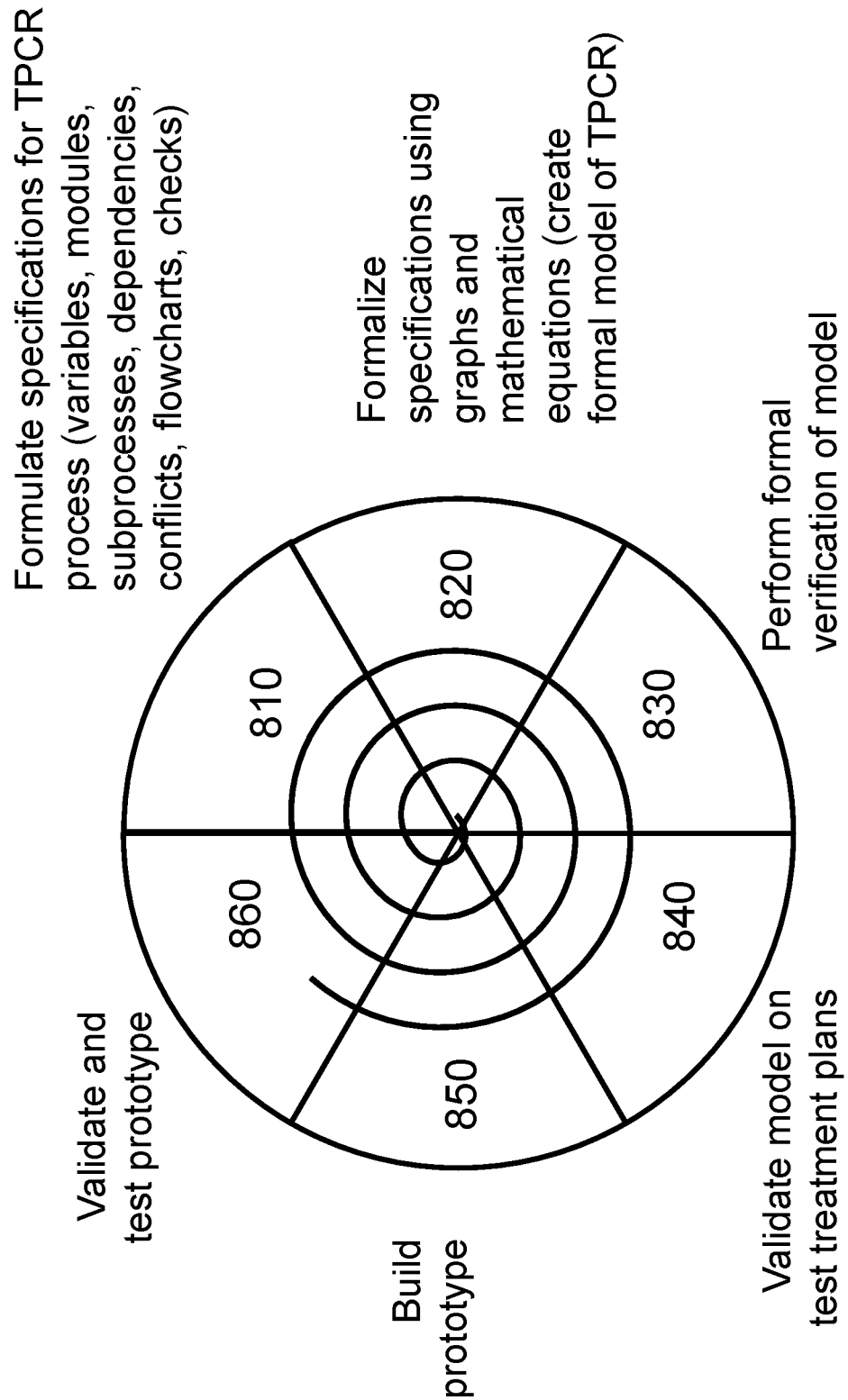
FIG. 8 illustrates a flow chart depicting an example method of preparing a model of the TPCR process in accordance with an embodiment of the present invention.

FIG. 8 illustrates a flow chart depicting an example method of preparing a model of the TPCR process in accordance with an embodiment of the present invention. An iterative, spiral technique is used to obtain the final model in accordance with the 6 steps described below.

In Step 810, the modules, sub-processes and variables describing the TPCR process are first defined followed by a definition of the dependencies and conflicts between the variables and the checks to be performed on the variables. For each of the variables, severity scores describing the seriousness of an error associated with that variable is also defined. The order in which the sub-processes are related to each other is described in a flowchart (FIG. 13) and the order in which the checks are performed, if performed sequentially, is described by a chart check priority table (Appendix B).

In Step 820, a formal model of the TPCR process is created from the specifications. That is, the specifications are formalized. This involves defining the allowed finite set of values for each of the variables and constraints in the form of equations that specify the allowed values for a group of variables within the context of the pre-defined dependencies. The specifications are formal in that they have a syntax, fall within a domain and can be used for inference. In Step 820, a directed graph embodying the dependencies between the variables is also created. An example of a directed graph obtained from the defined dependencies is shown in FIG. 14A. The directed graph allows the calculation of the connectivity of each variable, that is, the number of variables feeding into and out of the variable, thus providing information about the source of an error and how the error propagates through the chart check process.

In Step 830, a formal verification of the formal model is performed to demonstrate that the model is correct with respect to the specifications. The consistency and integrity of the specifications is verified by checking if the equations defining the constraints on the variables can be satisfied. This is achieved either through user-defined code or through existing software libraries.

In Step 840, the formal model is validated on test treatment chart examples. Validation involves determining if the formal model correctly describes the TPCR review process and is capable of identifying inconsistences in treatment charts. This step is achieved by running the model on test examples with known errors.

Once the model has been verified and validated, a prototype of the automated chart review program encompassing a graphical user interface is then built, tested and validated in Steps 850 and 860. Once it has been validated it is released for use.

Figure 9:
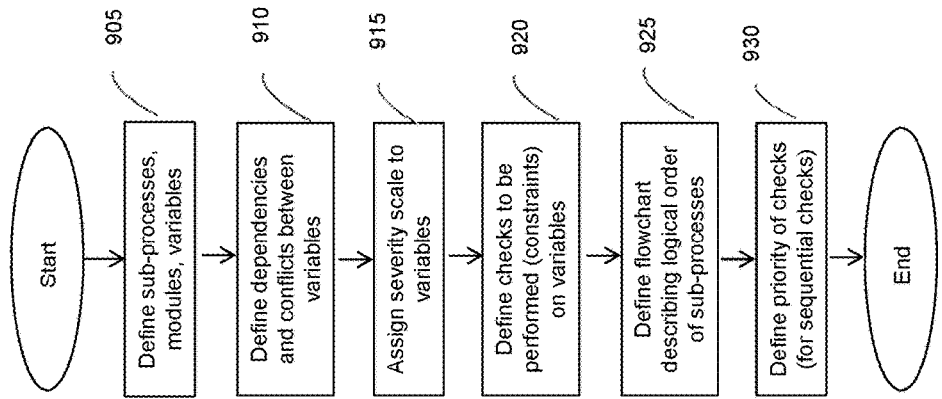
FIG. 9 is a flow chart depicting an example method of formulating the specifications for a TPCR process in accordance with an embodiment of the present invention.

FIG. 9 is a flow chart depicting an example method of formulating the specifications for a TPCR process in accordance with an embodiment of the present invention.

FIG. 9 provides a step-by-step breakdown of Step 1 in FIG. 8. The modules, sub-processes and variables describing the TPCR process are first defined 905. Examples of modules include Patient Manager, Treatment Planning System and Record and Verify. The Patient Manager module is also referred to as Documents module. As part of a standardization of the TPCR process, the model used here is based on emerging standards proposed by AAPM TG275. Additional variables and checks have been added based on conventions followed in leading clinics. In the embodiment, variables are named according to the functionality of the field they represent and contain a suffix consisting of an abbreviation for the module name. This naming convention enables a user to identify the location of an inconsistent variable. For instance, the variable representing the prescribed radiation dose in a document called Planning Intent located in Patient Manager is called PrescriptionDose_PM_PlanningIntent. Similarly, the variable representing the prescribed dose in the treatment planning system is named PrescriptionDose_TPS. We also define the datatype for the variables (boolean, string, float, integer, etc.) and their list of permissible values. Sub-processes represent different activities performed in the TPCR. An example listing of sub-processes and variables contained in these sub-processes is provided in Appendix A. The full model of the TPCR included 4 modules, 19 sub-processes and 337 variables (75 distinct).

Next, the dependencies and conflicts between all 337 variables are defined 910. Dependencies are a function among other factors of clinical practice, standardized practices in the field, the software modules used, the physical characteristics of the treatment machines, the imaging used and the physics of radiation dose calculation and treatment planning. For example, prescribed dose is a function of treatment site, the intent of the treatment, dose per fraction and number of fractions among other variables. Furthermore, prescribed dose should be consistent across modules. In this case, an example of a dependency would be PrescriptionDose_PM_PlanningIntent is dependent on TreatmentSite_PM_PlanningIntent, CourseIntent_PM_PlanningIntent, DosePerFraction_PM_PlanningIntent and NumberOfFractions_PM_PlanningIntent. To reflect consistency of variable values across modules, PrescriptionDose_TPS, PrescriptionDose_RV and PrescriptionDose_RV are said to be dependent on PrescriptionDose_PM_PlanningIntent. A conflict arises when the value of one variable precludes the value of another variable. An example of conflicting values of two variables is IMRT as the treatment modality and a 3D dose calculation point. A treatment modality of IMRT precludes the possibility of the dose calculation point being specified in 3D.

A severity score is pre-assigned to each variable 915 depending on the seriousness of an error associated with that variable and the potential to result in harm to a patient. Severity scores can be 0, 1 or 2, with zero indicating no harm, one indicating possible harm and 2 indicating a serious error leading to harm to a patient.

The checks to be performed on the variables to verify their consistency and integrity in the different sub-processes are represented by constraints that restrict the values of the variables relative to their dependent variables 920. For instance, although prescription dose may take a large set of values, its permissible values is restricted by treatment site.

The order in which the sub-processes are related to each other is described in a flowchart 925 (FIG. 13) and the order in which the checks are performed, if performed sequentially, is described by a chart check priority table 930 (Appendix B). The solution state for the variables is tracked by assigning states to the variables (Checked, Pending, Approved) as illustrated in the chart check priority table (Appendix B). The state of a sub-process is given by a flag output by that sub-process. The chart check priority table also provides information regarding the actions to follow by the user to resolve any identified inconsistencies. For instance, if there is a discrepancy in patient name across modules or if the planning intent, which contains the prescription, has not been approved by the physician, the user is advised to not proceed with the chart review until the correct patient has been identified and the planning intent has been approved.

Figure 10:
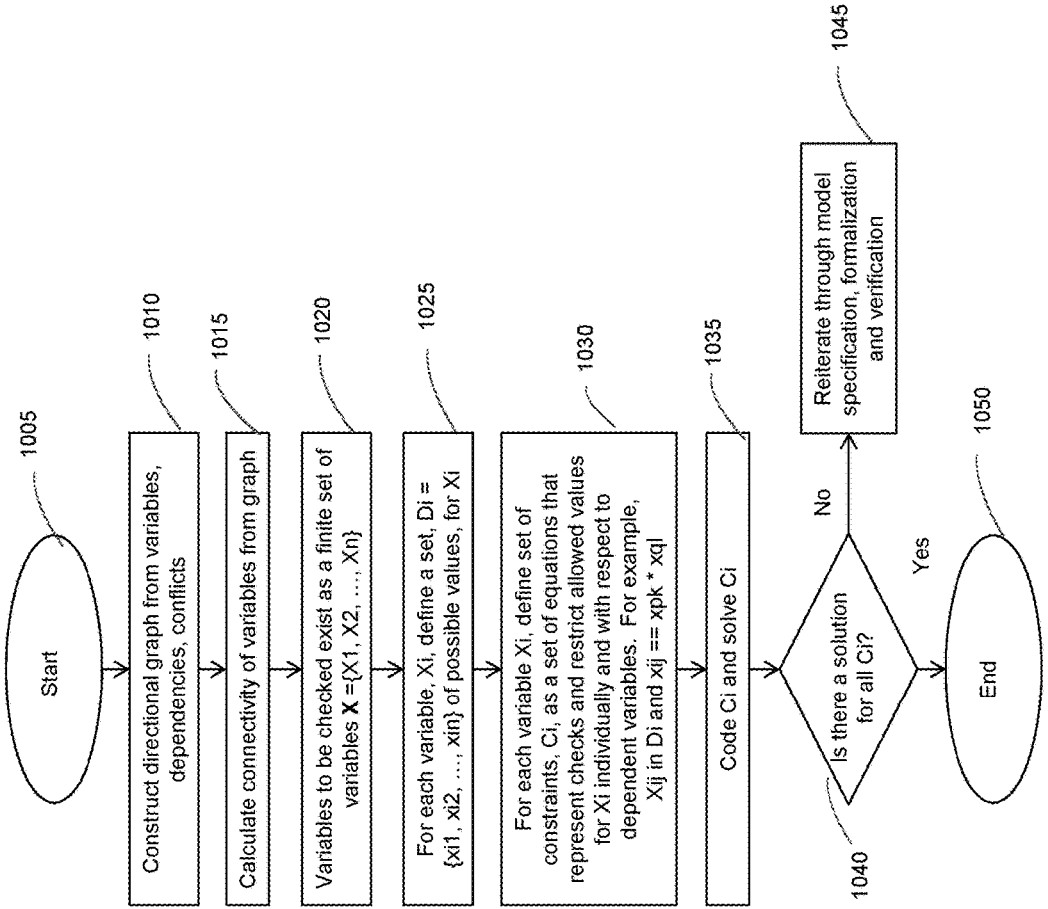
FIG. 10 is a flow chart depicting an example method of formalizing and verifying a TPCR process in accordance with an embodiment of the present invention.

FIG. 10 is a flow chart depicting an example method of formalizing and verifying a TPCR process in accordance with an embodiment of the present invention.

At the start 1005, a directed graph embodying the dependencies and conflicts between the variables is created 1010 from the adjacency matrix for the model, FIG. 14A. Each variable represents a node in the graph. The parents to a node in the graph give potential sources of error while the children (propagating variables) give a measure of impact of an error on other variables in the chart.

For each variable, the in connectivity and out connectivity are calculated using a breadth-first search procedure on the graph 1015.

The variables to be checked exist as a finite set of variables, Xi, that can each take an allowed finite set of values in a domain Di 905, 1020. For the example defined below addressing a subset of the 337 variables, Xi={TreatmentSite_PM_PlanningIntent, CourseIntent_PM_ PlanningIntent, TreatmentModality_PM_PlanningIntent, DoseFractionationType_PM_PlanningIntent, DosePerFraction_PM_PlanningIntent, NumberOfFractions_PM_PlanningIntent, PrescriptionDose_PM_PlanningIntent, PrescriptionDose_TPS, PrescriptionDose_RV}

For each variable, Xi, we then define a set Di of possible values for Xi 1025. For instance, for the subset of selected variables, the following allowable values are defined:
TreatmentSite_PM_PlanningIntent ∈{Brain, Brain LGG, Brain HGG, Lung NSCLC}
CourseIntent_PM_PlanningIntent ∈{Curative, Palliative}
TreatmentModality_PM_PlanningIntent ∈{3D, IMRT}
DoseFractionationType_PM_PlanningIntent ∈{Conventional, Hypo}
RadiationType_PM_PlanningIntent ∈{Electrons, Photons}
DosePerFraction_PM_PlanningIntent ∈{180, 200, 300, 100}
NumberOfFractions_PM_PlanningIntent ∈{5, 10, 30, 33}
PrescriptionDose_PM_PlanningIntent ∈{3000, 5000, 5400, 5940, 6600}

For each variable in the TPCR process, the checks to be performed are defined as constraints, Ci, that specify the allowed values for a group of variables within the context of the pre-defined dependencies 1030. An example set of equations related to prescription dose is given below. Here the symbol ∈ indicates that the variable or set of variables to the left of the symbol has a value or values, which are a member of the set shown to the right of the symbol. The equations below illustrate that PrescriptionDose_PM_PlanningIntent is dependent on TreatmentSite PM_PlanningIntent, CourseIntent_PM_PlanningIntent, TreatmentModalility PM_PlanningIntent, DoseFractionationType_PM_PlanningIntent, RadiationType PM_PlanningIntent, DosePerFraction PM_PlanningIntent, NumberOfFractions. PM_PlanningIntent and that PrescriptionDose should be consistent across the modules TPS and RV.

PrescriptionDose_PM_PlanningIntent=DosePerFraction_PM_PlanningIntent×NumberOfFractions_PM_PlanningIntent {TreamentSite_PM_PlanningIntent, CourseIntent_PM_PlanningIntent, TreatmentModality_PM_PlanningIntent, DoseFractionationType_PM_PlanningIntent,
RadiationType_PM_PlanningIntent, DosePerFraction_PM_PlanningIntent, NumberOfFractions_PM_PlanningIntent, PrescriptionDose_PM_PlanningIntent} ∈{(Brain, Palliative, 3D, Conventional, Photons, 300, 10, 3000), (Brain LGG, Curative, IMRT, Conventional, Photons, 180, 30, 5400)

(Brain HGG, Curative, IMRT, Conventional, Photons, 180, 33, 5940)

(Lung NSCLC, Curative, IMRT, Conventional, Photons, 200, 33, 6600)

(Lung NSCLC, Curative, IMRT, Hypo, Photons, 1000, 5, 50)}

PrescriptionDose_TPS=PrescriptionDose_PM_PlanningIntent
sPrescriptionDose_RV=PrescriptionDose_PM_PlanningIntent The set of equations is then solved 1035. A solution exists if all constraints can be satisfied 1040. If a solution exits, the formal specification of the model is complete 1050. Otherwise, the model parameters and constraints are adjusted and the model is reformalized 1045. If correctly specified, a solution exists because the model captures checks that are performed on a routine basis in the clinic.

Figure 11:
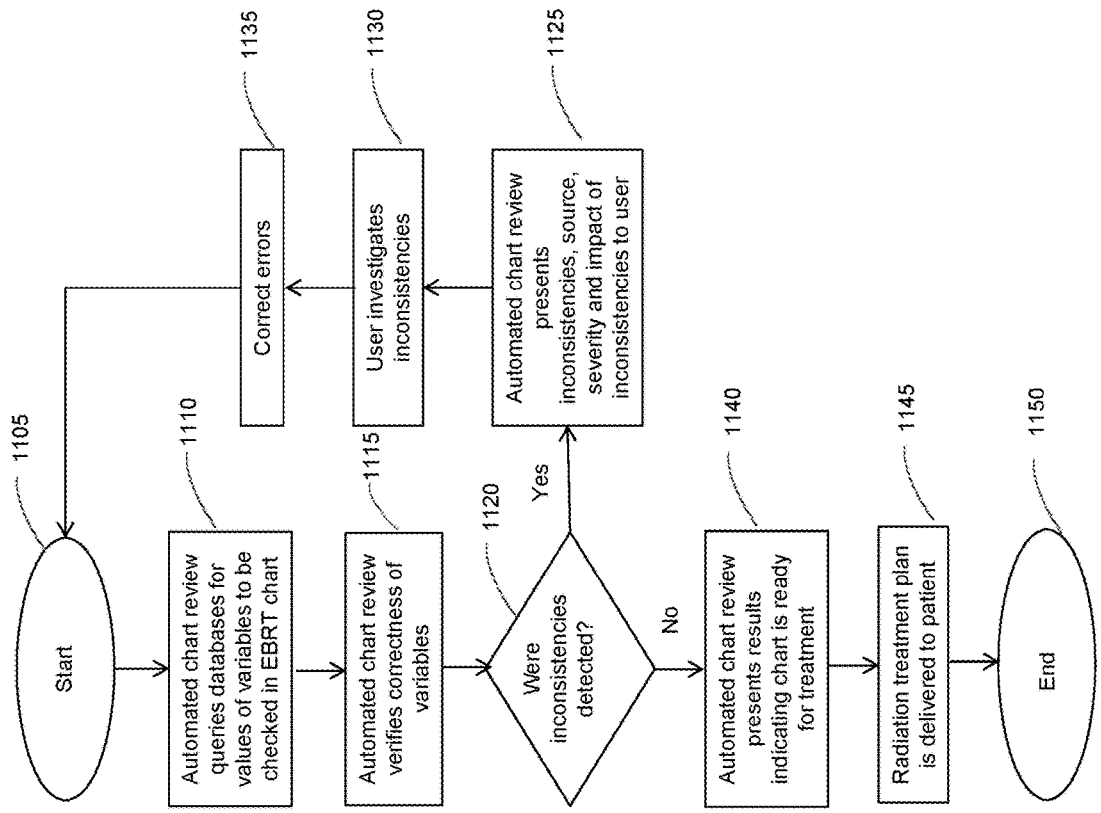
FIG. 11 is a flow chart depicting the process of automated chart review in accordance with an embodiment of the present invention.

FIG. 11 is a flow chart depicting the process of automated chart reviewer in accordance with an embodiment of the present invention.

In FIG. 11, at the start 1105, the automated chart reviewer first queries the databases associated with the different modules based on patient identity and parses the data and assigns values to the variables to be checked 1110. The chart review program then evaluates the correctness of the variables by evaluating them to see if they violate the constraints defined in the formal TPCR model 1115. If inconsistencies are detected in the values of the variables 1120, the automated chart review outputs the conflicting variables, the source of the inconsistency, the impact of that variable on variables downstream of that variable and the severity of a potential error 1125. An interlock on the treatment machine prevents the radiation beam from turning on for that patient. The impact of an inconsistency, and potential error, on other variables is determined from the out connectivity of that variable in the directed graph used within the solution. The inconsistencies are investigated 1130 and corrected 1135 the treatment chart and the chart reviewer is run again. If no conflicts or inconsistencies are detected, the user is informed that the treatment plan can be approved and delivered to the patient 1140. This enables the radiation plan to be loaded on the treatment machine and the radiation beam to be turned on for radiation delivery 1145. At this stage, the automated chart review is complete 1150.

Figure 12:
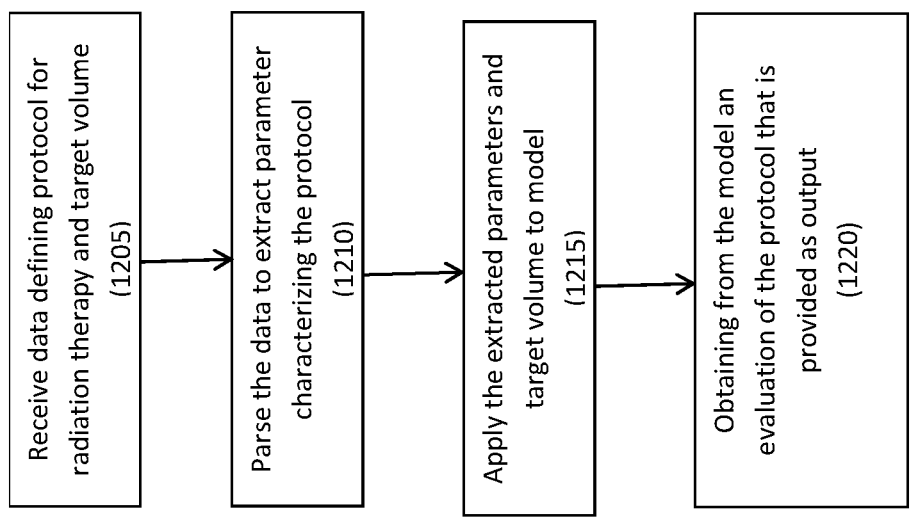
FIG. 12 illustrates a flow chart depicting evaluation of a protocol for radiation treatment using a model in accordance with an embodiment of the present invention.

FIG. 12 illustrates a flow chart depicting evaluation of a protocol for radiation treatment using a model in accordance with an embodiment of the present invention. In FIG. 9, the chart review program (a computer process), receives 1205 data defining a protocol (or treatment plan, such as RT chart) for radiation therapy and target volume. The method may be performed continuously, in real-time, while formulating the protocol for radiation, or on the protocol after formulation of the protocol is complete. The program is executed by a computer system, such as shown in FIGS. 3A and 3B. The data may be automatically retrieved by querying one or more modules (such as shown in FIG. 7) based on identity of the patient. The program parses 1210 the data to extract parameters characterizing the protocol.

The program then applies 1215 the extracted parameters and the target volume to a model that represents relationships among the processes (also called sub-processes) and variables pertinent to execution of the protocol in a patient. The model may be a decomposed TPCR process specification, including the processes, the variables, and modules (such as shown in FIG. 6). Each of the sub-processes includes at least one of the variables, and the relationships include dependencies, constraints, and conflicts among the sub-processes and variables. The dependencies of the variables may be represented in a directed graph, as illustrated in FIG. 14A, which show connectivity between the variables.

Figure 13:
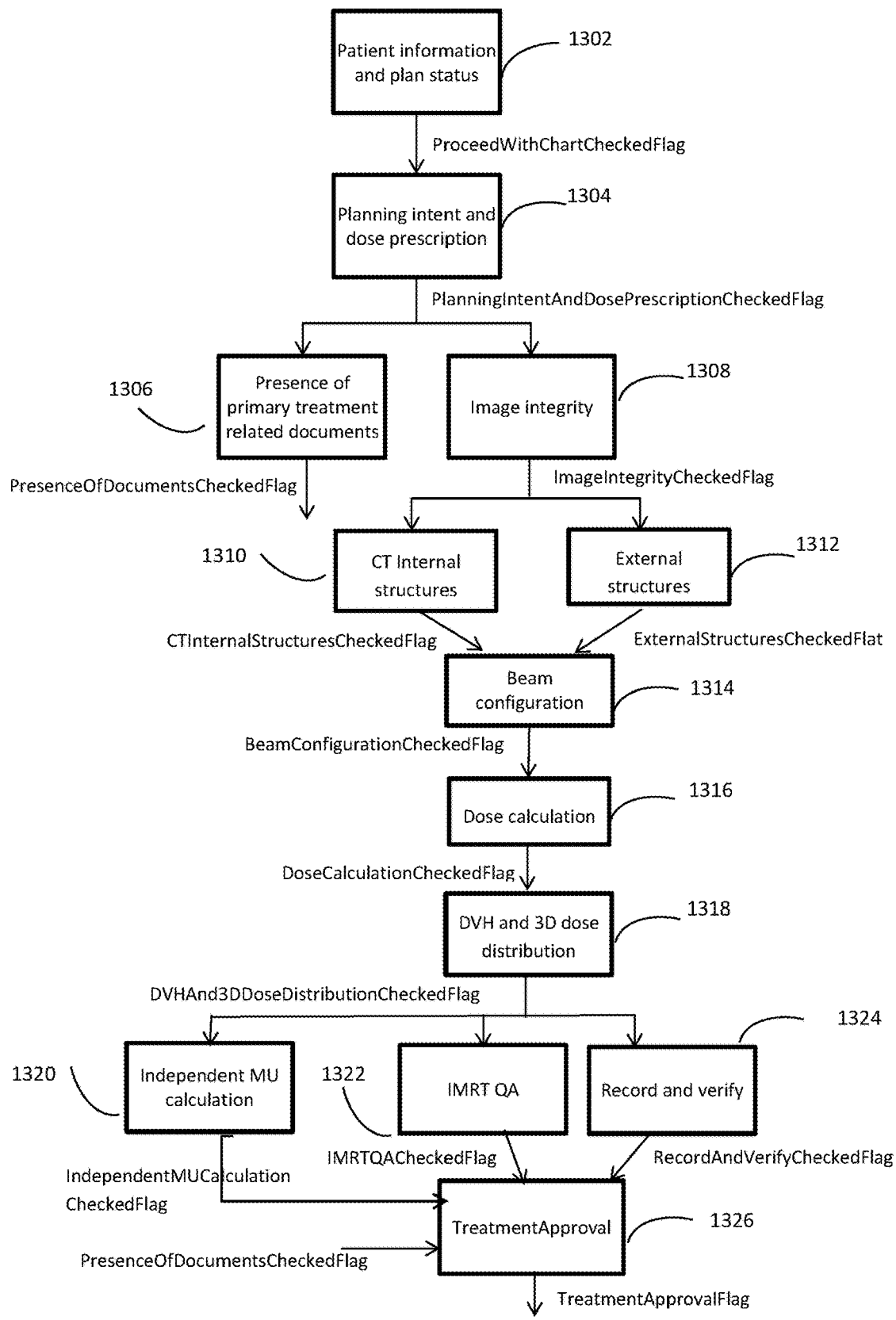
FIG. 13 illustrates a flow chart depicting an example method of sequential checking of sub-processes in accordance with an embodiment of the present invention.

For each sub-process, the program checks a subset of the parameters against corresponding variables in the sub-process, and determines any conflicts (logical inconsistencies or errors) pertinent to the subset of parameters. Appendix B shows example checks performed with respect to variables associated with sub-processes. An inconsistency occurs between two variables when the value taken by one variable (corresponding to a first parameter) precludes a value taken by a second variable (corresponding to a second parameter). That is, a permissible range of values is assigned to each variable, and an inconsistency occurs if setting one variable to the value in the corresponding parameter would cause a dependent variable to go outside its permissible range. In embodiments, the model specifies an optimal order and priority for checking the variables in the sub-process. If the evaluation method is being performed on a completed formulated protocol, program may be configured to check the subset of parameters, with respect to each sub-process, either simultaneously (in parallel) or sequentially. FIG. 13 illustrates an example logic flow of sequential checking of the sub-processes. In embodiments, the program may determine an optimal path for checking the variables in a particular sub-process and across the sub-processes. The program tracks the state of the checking by assigning states to the sub-processes and variables.

The program then obtains 1220 from the model an evaluation of the protocol and providing the evaluation as an output. For example, when checking the subset of parameters, if a conflict occurs with respect to a particular variable, the program determines the severity of the conflict. To do so, the program references a pre-defined severity assigned to that particular variable. The program may cause graphical display of the subset of parameters and the corresponding severities for analysis by a user. The graphical display may order the subset of parameters based on the severities.

For another example, if a conflict occurs with respect to a particular variable, the program determines a set of determining (i) a set of source variables that are a cause of the conflict, and (ii) a set of propagation variables that are affected by the conflict. To do so, the program locates the node corresponding to the particular variable in the directed graph, and determines, based on the connectivity with respect to that node, the variables that are sources to that node (i.e., the source variables) and the variables that propagate from that node (i.e., the propagation variables). The program may cause graphical display of the set of source variables and the set of propagation variables for analysis by the user.

FIG. 13 illustrates a flow chart depicting an example method of sequential checking of sub-processes in accordance with an embodiment of the present invention.

FIG. 13 expands upon Step 810 of FIG. 8 regarding specifying the order in which example sub-processes are related to each other. Each sub-process describes a particular activity or feature of the TPCR process. The sub-processes include the variables of patient treatment plans (for example an RT chart) describing these activities and features and the checks to be performed on these variables. An example listing of sub-processes and variables contained in these sub-processes is provided in Appendix A.

The order in which a sample of sub-processes are related to each other is required for sequential checking of the sub-processes and for correction of inconsistencies in the treatment chart evaluated by the automated chart review. For example, "patient information and plan status" 1302 describes the checks associated with verifying that parameters describing the patient name and medical record number, treatment plan name, treatment course number and whether the treatment chart is ready to be reviewed. "Planning intent and dose prescription" verifies that the radiation dose and treatment prescription information 1030 entered by the physician is correct and consistent across modules 1304. "Presence of primary treatment related documents" 1306 verifies that all documents necessary for treatment planning, treatment delivery and providing documentation of the patient's treatment plan are present in the treatment chart. "Image integrity" 1308 verifies that the quality of the images and conformance to the physician's specifications. In "CT internal structures" 1310, the presence of contours delineating the anatomical structures listed in the planning intent document is verified for consistency and correctness in the treatment planning system. Similarly, "External structures" 1312 verifies the integrity and consistency of variables linked to the presence of immobilization devices, medical devices, prosthesis, etc. in the Documents module and treatment planning system. "Beam configuration" 1314 verifies the correctness of variables describing the ionizing radiation beams that are used to target the tumor and from which the radiation dose distribution is calculated. "Dose calculation" 1316 verifies the integrity of variables describing the dose calculation algorithm and associated parameters. "DVH and 3D dose distribution" 1318 evaluate parameters describing the quality of the radiation dose distribution and the dose volume histogram calculated by the treatment planning system. An independent verification of the accuracy of the dose distribution calculated by the treatment planning system is required. "Independent MU calculation" 1320 verifies the integrity and consistency of the input and output of module used to perform the independent MU calculation.

An independent physical measurement of the planned radiation dose is also required to ensure that the calculated radiation distribution is deliverable on the treatment machine. "IMRT QA" verifies that the measurement was performed correctly and that the output of the measurement is within a pre-defined and acceptable tolerance 1322. Once the planning of the treatment is completed in the treatment planning system, the treatment plan is transferred to the record and verify system. Record and verify also contains treatment imaging instructions and patient scheduling information. This sub-process verifies that the information in the record and verify system is correct and consistent with that in the treatment planning system and documents module 1324. Finally, once all the sub-processes have evaluated their respective variables and if no inconsistencies are detected, the treatment plan is approved for treatment and delivered on the treatment machine 1326.

Figure 14B:
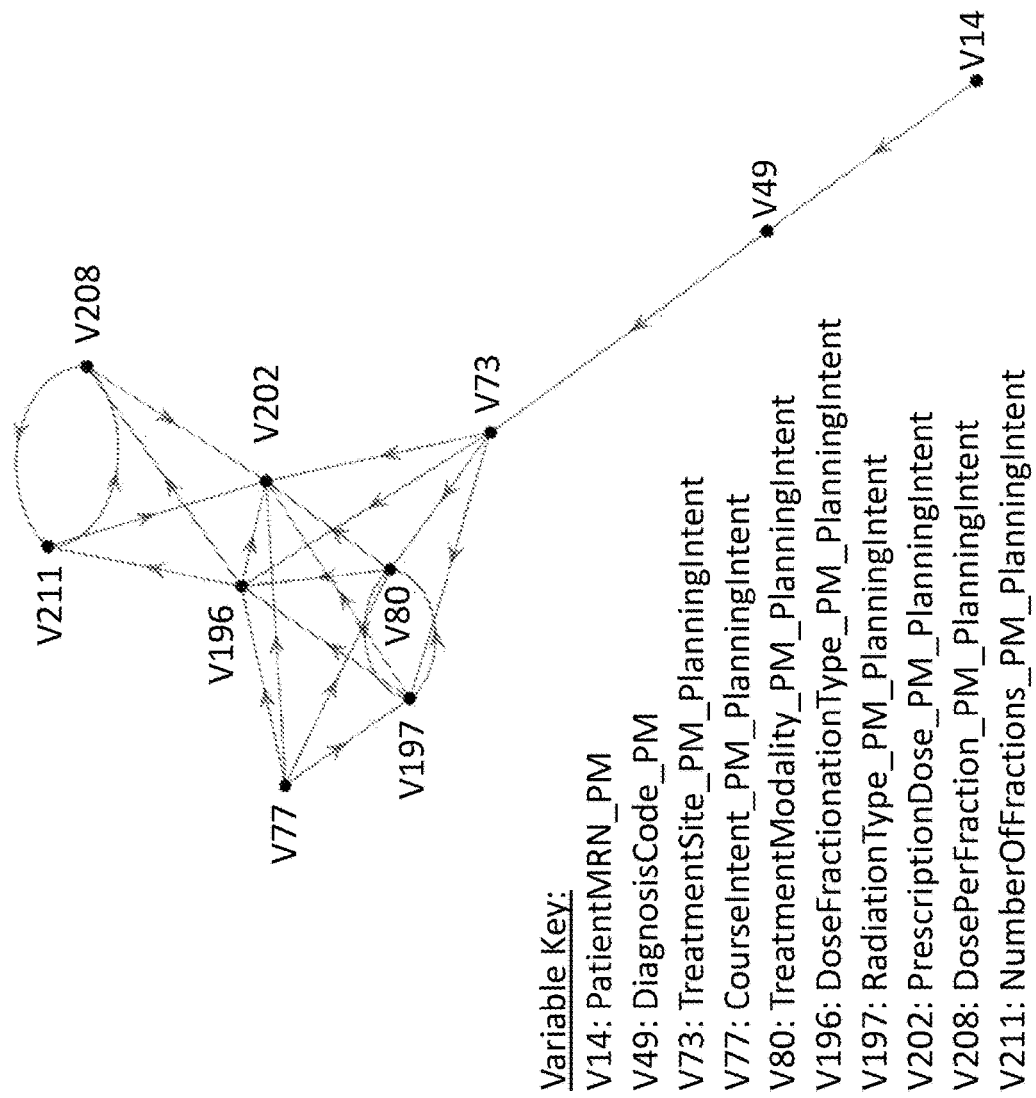

FIGS. 14A-14B is a directed graph and sub-graph of dependencies with a model of a TPCR process in accordance with an embodiment of the present invention.

The model may be a decomposed TPCR process specification including the sub-processes, the variables, and modules (such as shown in FIG. 6). Each of the sub-processes includes at least one of the variables, and the relationships include dependencies and conflicts among the variables. A directed graph is created from an adjacency matrix representing the relationships between variables. The directed graph of the TPCR process is an ordered pair (V, E) where V is a set of whose elements are called vertices, nodes or points as illustrated in FIG. 14A. Here, each node, Vi, is directly mapped a variable, Xi, in the set of variables, X (FIG. 10), being evaluated. E is a set of edges denoting an ordered pair of vertices called arrows, directed edges or directed lines. A directed edge or arrow going, for example, from vertex Vi to Vj, exists if Xj is dependent on Xi. An arrow (Vi, Vj) is considered to be directed from Vi to Vj. Vi is called the head of the arrow and Vj is called the tail of the arrow. The indegree of variable Xi is defined by the number of arrow heads going into Vi and the outdegree of variable Xi is defined by the number of tails adjacent to Vi. When a variable Xi is found to be inconsistent, the possible sources of the inconsistency at the first level are determined from the heads of all arrows leading directly to Xi. The possible sources of error at a deeper level can be found recursively in the same manner. The set of vertices so identified are called the parent vertices of Vi and the corresponding variables give all possible sources of inconsistency for Xi. Similarly, the way in which an error or inconsistency propagates, or the set of all variables impacted by Xi is found recursively from the tails of all arrows leading out of Xi and so forth. The variables associated with the tails of the arrows are called children. The level of the children with respect to Xi is determined by how many times removed the arrow tails are from Vi. The in connectivity is obtained by summing the indegree of variable Xi at all levels. The out connectivity is obtained by summing the outdegree of variable Xi at all levels. The out connectivity gives the total number of variables directly and indirectly impacted by Xi. The priority in which an error is corrected can be partly determined from its out connectivity and the order of the sub-process to which it belongs. For example, priority should be variables with high out connectivity and which appear early in the sub-processes should be given priority since they impact many variables.

FIG. 14B illustrates a subset of the directed graph illustrating the parents for PrescriptionDose_PM_PlanningIntent (V202). This sub-graph includes an illustration of the dependencies defined in 910. At level 1, the parent variables are TreatmentSite_PM_PlanningIntent (V73), CourseIntent_PM_PlanningIntent (V77), TreatmentModality_PM_PlanningIntent (V80), RadiationType_PM_PlanningIntent (V197), DosePerFraction_PM_PlanningIntent (V196) and NumberOfFractions_PM_PlanningIntent (V211). DiagnosisCode_PM (V49) is a parent at level 2 and PatientMRN_PM (V14) is a parent at level 3. An inconsistency in PrescriptionDose_in the Planning Intent document in the Patient Manager module may be identified by an unsatisfied constraint with respect to these variables.

Figure 15B:
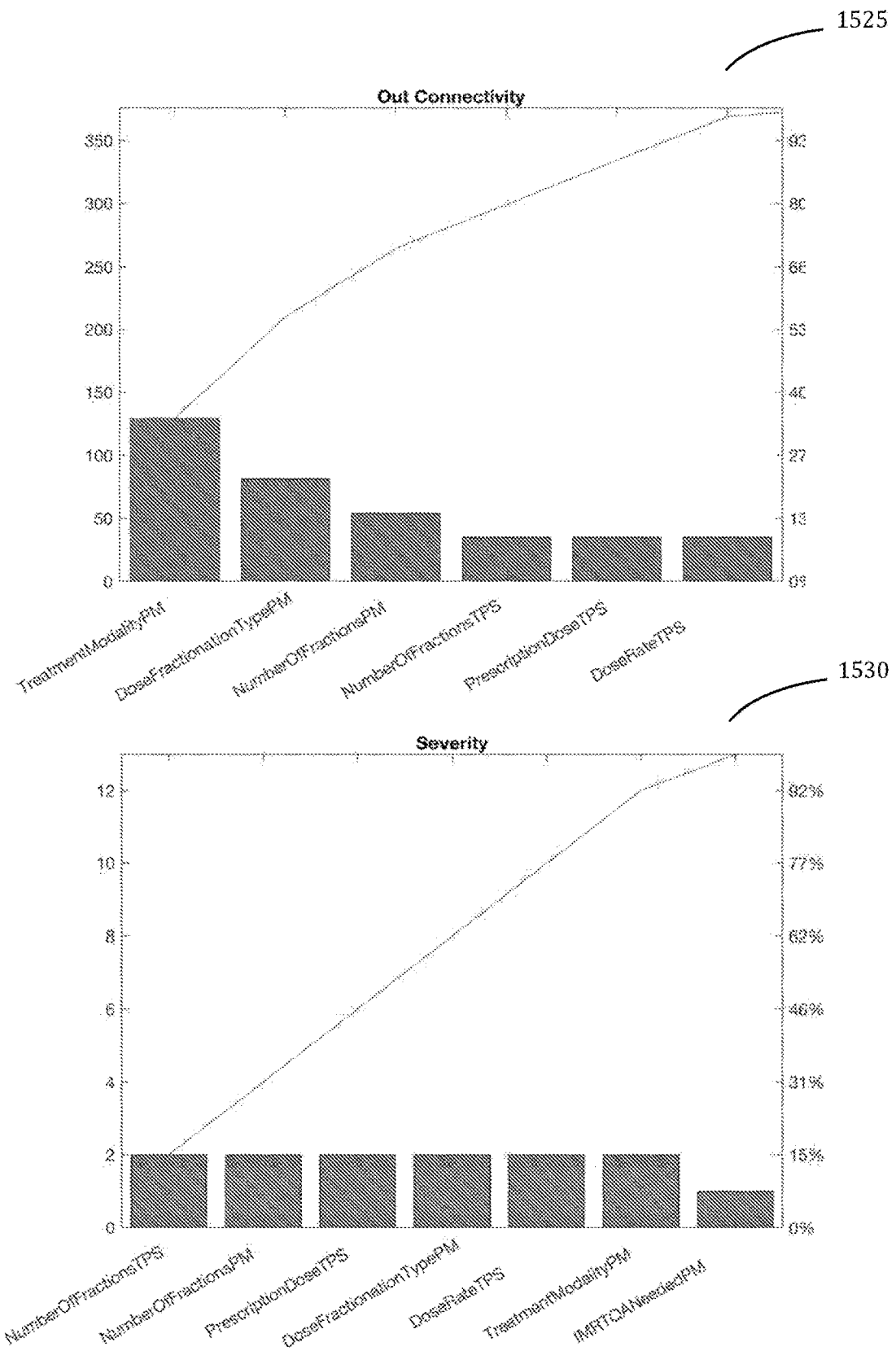

FIGS. 15A-15B illustrate automated chart review reports generated from evaluating a patient's treatment protocol in accordance with an embodiment of the present invention.

After the automated chart review program has executed, the user has an option to generate a report 1610 describing the output of the program. The report contains the patient identification information and treatment plan name and course number 1505. The first table in the report states whether the radiation plan is approved for treatment 1510. If the plan is not approved, the report also states the number of constraints violated, the number of variables in the RT chart which were found to be inconsistent, according to the relationships and constraints described in FIG. 8, an impact score, which represents the cumulative out connectivity score and a cumulative severity score. The second table gives a summary of the conflicts (or inconsistencies) detected by the automated chart review program 1515. Each inconsistency detected is reported in a separate row. This table provides information about the context in which the inconsistencies arise. That is, it describes what constraints were violated and by so doing provides the user with contextual information about the inconsistency. An inconsistency in a variable indicates that an error may be present in that variable. The inconsistency can then be further investigated by the user to determine whether an error was present in the inconsistent variable.

The third table provides details regarding the variables that were found to be inconsistent, ranked in descending order of out connectivity and severity 1520. The first column lists the values of the variables. The second and third column list the module and sub-process that the variables belong to. For instance, in this example, IMRT QA needed has a value of Yes and belongs to Module Patient Manager and Sub-process IMRT QA. This information is required in order for the user to know where to correct an error, if present. The fifth column gives the out-connectivity of the variables as described in FIG. 14A. The out-connectivity lists how many variables are dependent on a given variable, both directly and indirectly. This number is obtained using a graph traversal algorithm. The out-connectivity describes how an error propagates or how many variables are impacted by an error in a given variable. For Treatment Modality, the out connectivity is 129. The severity of a potential error associated with an inconsistent variable is listed in column 6. Here, IMRT QA needed has a severity score of 2.

The graphs in FIG. 15B illustrate Pareto charts of the out connectivity 1525 and severity scores 1530 for the variables found to be inconsistent. The Pareto chart contains both bar and line graphs for the out connectivity and severity associated with the variables. The bar graph represents the values ranked in descending order while the line graph represents a cumulative total of the values. The pareto chart for out connectivity 1525 illustrates the inconsistent variables and the number of other variables they impact in the treatment chart. It also gives a cumulative total of the number of variables impacted by the detected inconsistent variables. Similarly, the same information is provided with respect to the severity scores 1530 associated with the inconsistent variables. This information is useful for the determination of the order in which to investigate and correct the detected inconsistencies. For instance, it is desirable to first investigate and correct variables with a high out connectivity and high severity score.

Figure 16:
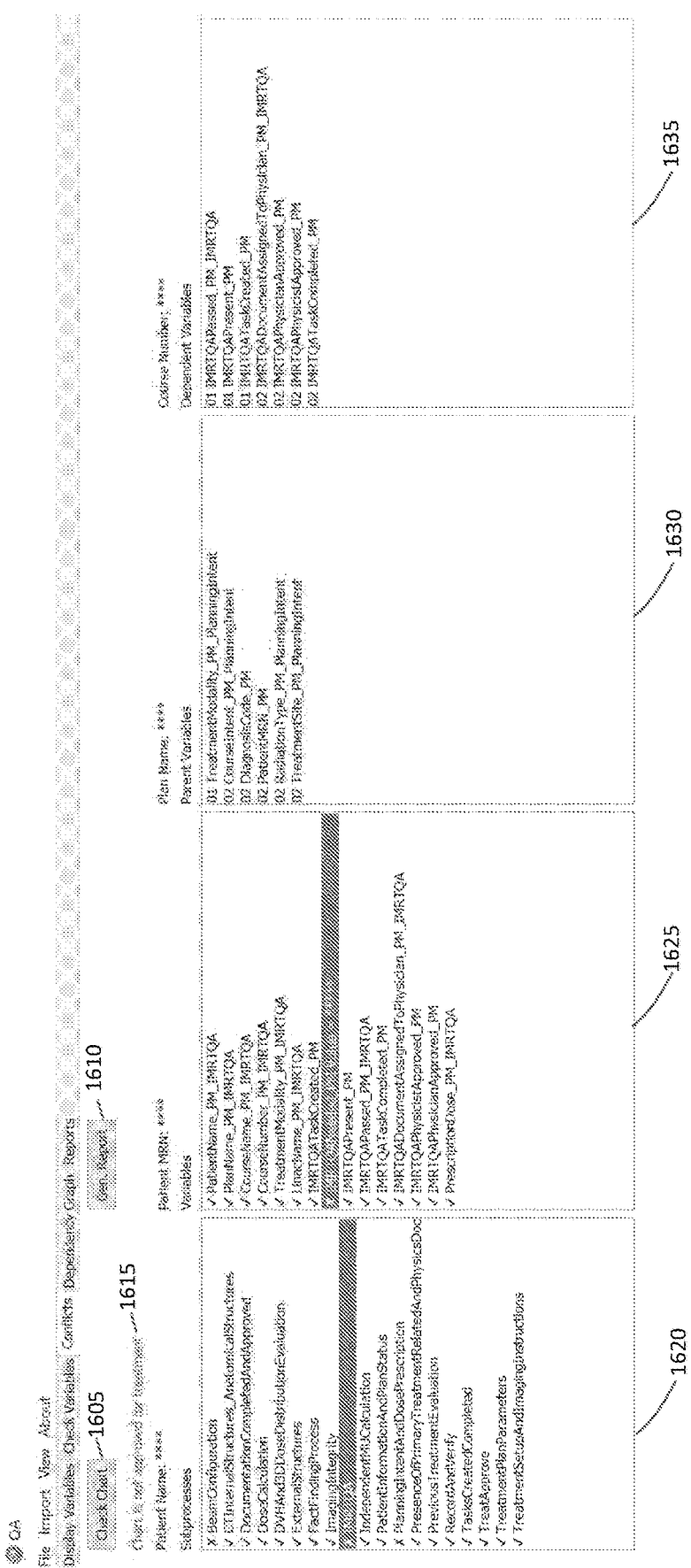
FIG. 16 illustrates an example of a graphical user interface and output returned on conflicts from the automated chart review program in accordance with an embodiment of the present invention.

FIG. 16 illustrates an example of a graphical user interface and output returned on conflicts from the automated chart review program in accordance with an embodiment of the present invention.

The chart review process 1605 is executed by a computer system, such as shown in FIGS. 3A and 3B. The data may be automatically retrieved by querying one or more modules (such as shown in FIG. 7) based on identity of the patient. As described in FIG. 12, the program parses 1210 the data to extract parameters characterizing the protocol. The program then applies 1215 the extracted parameters and the target volume to a model that represents relationships among the processes (also called sub-processes) and variables pertinent to execution of the protocol in a patient. In the example of FIG. 16, the program finds all inconsistencies across all variables and sub-processes simultaneously. After execution, the program lists the status for the start 1615 with further detailed information being available 1610. For each sub-process, the program lists the status of the sub-process 1620 with either a tick indicating that that no inconsistencies were found in that sub-process and all variables are correct or a cross indicates that variables in that sub-process were inconsistent. The user can navigate through the listed sub-processes by clicking on them. Clicking on a sub-process will show the variables belonging to that sub-process and their value in an adjacent window 1625. The automated chart review program indicates the status of the evaluation of the variables 1625 through ticks and crosses. A tick next to a variable indicates that it is correct while a cross indicates an inconsistency. The parents 1630, that is the possible source of an inconsistency for a given variable is found by clicking on that variable. The list of parents for that variable is obtained by traversing the directed graph FIG. 14A. Parent variables with level 1 are directly connected to the variable while variables at higher levels are indirectly connected with the degree of removal from the variable being examined increasing with level number. The impact of a given variable on other variables in the treatment chart is found by clicking on that variable. This produces a list of children 1635 of that variable. The list of children (propagation) variables for a given variable is found by traversing the directed graph FIG. 14A. Similarly, the number denoting the level of a child variable denotes how many times removed it is from the variable being examined. Note that the parents and children do not necessarily belong to belong to the same sub-process as the variable being examined.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, networker, or locator.) Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), pre-loaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

While the invention has been particularly shown and described with reference to specific embodiments, it will be understood by those skilled in the art that various changes in form and detail may be made therein without departing from the spirit and scope of the invention as defined by the appended clauses. While some of these embodiments have been described in the claims by sub-process steps, an apparatus comprising a computer with associated display capable of executing the sub-process steps in the claims below is also included in the present invention. Likewise, a computer program product including computer executable instructions for executing the sub-process steps in the claims below and stored on a computer readable medium is included within the present invention.

The embodiments of the invention described above are intended to be merely exemplary; numerous variations and modifications will be apparent to those skilled in the art. All such variations and modifications are intended to be within the scope of the present invention as defined in any appended claims.

REFERENCES

[1] Chen G, Li X. Development of a QA software tool for automatic verification of plan data transfer and Delivery. Med Phys. 2012 June; 39 (6 Part 12): 3750

[2] Covington E L, Chen X, Younge K C, Lee C, Matszak M M, Kessler M L, Keranen W, Acosta E, Dougherty A M, Filpansick S E, Moran J M. Improving treatment plan evaluation with automation. J Appl Clin Med Phys. 2016 Nov. 8:17(6): 6322

[3] Gopan O, Zeng J, Novak A, Nuflot M, Ford E. The effectiveness of pretreatment physics plan review for detecting errors in radiation therapy. Med Phys. 2016 September; 43(9):5181

[4] Holdsworth C, Kukluk J, Molodowitch C, Czerminska M, Hancox C, Cormack R A, Beaudette K, Killoran J H. Competerized system for safety verification of external beam radiation therapy planning. Int J Radiat Oncol Biol Phys. 2017 Jul. 1:98(3):691-698

What is claimed is:

1. A computer-implemented method of evaluating a patient treatment chart and a protocol for a radiation therapy for a target volume of a patient, the computer-implemented method using a computer system executing software instructions establishing computer processes comprising:

applying, to a model, the target volume of the patient and parameters characterizing the protocol, wherein the model (i) represents relationships including dependencies among variables pertinent to an execution of the protocol in the patient, and (ii) represents for each variable of the variables other variables that influence each variable of the variables, and other variables that are influenced by each variable of the variables;

wherein applying the target volume of the patient and the parameters to the model includes checking a subset of the parameters against corresponding variables of the variables to determine any of conflicts and inconsistencies, which are collectively referred to as incongruities pertinent to the subset of the parameters; and obtaining from the model an evaluation of the protocol and providing the evaluation as an output.

2. The computer-implemented method in accordance with claim 1, wherein the relationships among the variables include the dependencies, constraints, and the incongruities among the variables.

3. The computer-implemented method in accordance with claim 2, further comprising querying a database system having data for a subset of the variables to retrieve data for at least one variable of the variables.

4. The computer-implemented method in accordance with claim 1,
wherein the variables represent at least three members selected from the group consisting of: a patient identification (MRN), a patient name, a diagnosis code, a treatment site, a course name/number, a course intent, a plan name, a prescribed dosage, a number of fractions, a target volume, a dose to a gross tumor volume, a dose rate, a treatment modality, a gross tumor volume, a clinical target volume, a planning target volume, organs at risk, dose constraints, a beam energy, a beam configuration, a dose calculation algorithm, a dose distribution, a dose volume histogram, a patient image, a linear accelerator, an independent MU calculation, an IMRT QA, a plan status, and combinations thereof.

5. The computer-implemented method in accordance with claim 1,
wherein the computer processes further comprise:
building the model by decomposing a patient treatment process into the variables.

6. The computer-implemented method in accordance with claim 5,
wherein the computer processes further comprise:
preparing the model for performing evaluations on the protocol, including: formalizing the model by converting the model into a series of equations; and performing a verification on the model by solving the series of equations using a computer-aided verification.

7. The computer-implemented method in accordance with claim 6,
wherein the computer processes further comprise:
applying sample protocols for a radiation therapy to the model using the computer-aided verification to determine a validity of the model.

8. The computer-implemented method in accordance with claim 1,
wherein the computer processes further comprise:
automatically retrieving the parameters of the protocol by querying based on an identity of the patient.

9. The computer-implemented method in accordance with claim 1,
wherein checking the subset of the parameters further includes:
determining an optimal order and priority for the checking the subset of the parameters.

10. The computer-implemented method in accordance with claim 9,
wherein checking the subset of the parameters further comprises:
checking the set of the parameters according to a member of the group consisting of: continuously, in real-time, while formulating the protocol for the radiation therapy; on the protocol after a formulation of the protocol is complete; and combinations thereof.

11. The computer-implemented method in accordance with claim 10, further comprising applying the parameters and the target volume of the patient to the model simultaneously or sequentially.

12. The computer-implemented method in accordance with claim 1,
wherein checking the subset of the parameters further includes:
determining whether each parameter of the parameters causes a conflict with a value set for any of other parameters of the parameters.

13. The computer-implemented method in accordance with claim 1,
wherein checking the subset of the parameters further includes:
for each parameter of the subset of the parameters, determining a severity of a conflict based on a predefined score assigned to a variable corresponding to each parameter of the subset of the parameters; and
causing a graphical display of the subset of the parameters and corresponding severities for an analysis.

14. The computer-implemented method in accordance with claim 1,
wherein checking the subset of the parameters further includes:
determining (i) a set of source variables that are a cause of a conflict, and (ii) a set of propagation variables that are affected by the conflict; and
causing a display of (i) the set of source variables and (ii) the set of propagation variables for an analysis.

15. The computer-implemented method in accordance with claim 1, further comprising determining an impact of a conflict based on an outconnectivity of a variable or a set of propagation variables that are affected by the conflict.

16. The computer-implemented method in accordance with claim 1, wherein checking the subset of the parameters further includes:
modeling relationships among the variables in a directed graph such that the directed graph represents, for each variable of the variables, other variables that influence each variable of the variables, and other variables that are influenced by each variable of the variables;
determining a variable associated with a given parameter of the subset of parameters; and
analyzing a relationship of the determined variable in the directed graph to locate (i) a set of source variables, which influence each variable of the variables, and (ii) a set of propagation variables that are influenced by each variable of the variables.

17. The computer-implemented method in accordance with claim 1,
wherein checking the subset of the parameters further includes:

tracking the evaluation of the protocol by assigning states to the variables pertinent to the execution of the protocol in the patient.

18. The computer-implemented method in accordance with claim 1, further comprising using a graph-theory to identify paths through the variables that minimize a number of dependencies, the incongruities, and stop-start cycles.

19. The computer-implemented method in accordance with claim 18, further comprising determining a finite state system based on the paths, where a next step after each variable of the variables is evaluated is based on accumulated histories.

20. The computer-implemented method in accordance with claim 19, further comprising using machine learning for any of an automated chart review and an error correction based on the finite state system.

21. The computer-implemented method in accordance with claim 18, further comprising assigning a probability to each next step to provide a stochastic process.

22. The computer-implemented method in accordance with claim 1, in which the step of providing the evaluation as the output includes identifying any of a priority and an order in which an error is corrected is based on one or more of an impact of the error, a severity of the error, and an ordering of the error in a patient treatment process.

23. The computer-implemented method in accordance with claim 1, further comprising an automated risk analysis and an evaluation based on one or more combinations of information pertaining to an error impact and an error severity.

24. The computer-implemented method in accordance with claim 1, in which the step of providing the evaluation as the output includes identifying where in a patient treatment process to correct one or more errors.

* * * * *